US007432061B2

(12) United States Patent
Moss et al.

(10) Patent No.: US 7,432,061 B2
(45) Date of Patent: Oct. 7, 2008

(54) ASSAYS FOR MEASURING MATRIX METALLOPROTEINASE ACTIVITIES

(75) Inventors: Marcia Lynn Moss, Apex, NC (US); Fred H. Rasmussen, Apex, NC (US); Michael P. Vitek, Apex, NC (US)

(73) Assignee: BioZyme, Inc., Apex, NC (US)

( * ) Notice: Subject to any disclaimer, the term of this patent is extended or adjusted under 35 U.S.C. 154(b) by 359 days.

(21) Appl. No.: 10/449,659

(22) Filed: Jun. 2, 2003

(65) Prior Publication Data

US 2003/0229005 A1 Dec. 11, 2003

Related U.S. Application Data

(60) Provisional application No. 60/384,135, filed on May 31, 2002.

(51) Int. Cl.

| | |
|---|---|
| ***G01N 33/53*** | (2006.01) |
| ***A61K 38/00*** | (2006.01) |
| ***C07K 2/00*** | (2006.01) |
| ***C07K 4/00*** | (2006.01) |
| ***C07K 5/00*** | (2006.01) |
| ***C07K 7/00*** | (2006.01) |
| ***C07K 14/00*** | (2006.01) |
| ***C07K 16/00*** | (2006.01) |
| ***C07K 17/00*** | (2006.01) |

(52) U.S. Cl. ........................ 435/7.1; 435/810; 530/300

(58) Field of Classification Search ....................... None
See application file for complete search history.

(56) References Cited

U.S. PATENT DOCUMENTS

| | | | | |
|---|---|---|---|---|
| 6,030,792 | A | 2/2000 | Otterness et al. | 435/7.1 |
| 6,127,139 | A | 10/2000 | Te Koppele et al. | 435/24 |
| 2002/0061569 | A1* | 5/2002 | Haselbeck et al. | 435/183 |
| 2003/0087863 | A1* | 5/2003 | Martignetti et al. | 514/44 |
| 2003/0180877 | A1* | 9/2003 | Deleersnijder et al. | 435/69.1 |

FOREIGN PATENT DOCUMENTS

| | | | |
|---|---|---|---|
| EP | WO 01/81581 A2 | * | 4/2001 |
| WO | WO 02/051444 | * | 7/2002 |

OTHER PUBLICATIONS

GenBank Accession No. A54808, May 7, 1999.*
GenBank Accession No. E64716, Sep. 29, 1999.*
GenBank Accession No. B71803, Sep. 29, 1999.*
Attwood et al. The Babel of Bioinformatics. Science. 290:471-473.*
Skolnik et al. 'From genes to protein structure and fucntion: novel applications of computational approaches in the genomic era.' Trends in Biotech. 18:34-39, 2000.*
Beekman B. et al., Highly Increased Levels of Active Stromelysin in Rheumatoid Synovial Fluid Determined by a Selective Fluorogenic Assay (1997), *FEBS Letters* 418: 305-309.
Beekman B. et al., Fluorogenic MMP Activity Assay for Plasma Including MMPs Complexed to $\alpha_2$-Macroglobulin (1999), *Annals N.Y. Acad. of Sci*. 878: 150-158.
Beekman B., et al., Convenient Fluorometric Assay for Matrix Metalloproteinase Activity and its Application in Biological Media, (1996), *FEBS Letters* 390: 221-225.
Bode W., et al. The Metzincin-Superfamily of Zinc-Peptidases (1996), *Intraellular Protein Catabolism* 1-11, Suzuki and Bond (eds.), Plenum Press, NY.
Deng S., et al., Substrate Specificity of Human Collagenase 3 Assessed Using a Phage-Displayed Peptide Library (2000), *Jour. Biol. Chem*. 275(40): 31422-31427.
Chen, et al. A Unique Substrate Recognition Profile for Matrix Metalloproteinase-2*, (2002) *Jour. Biol. Chem*., 277(6): 4485-4491.
Clark Billinghurst R., et al., Enhanced Cleavage of Type II Collagen by Collagenases in Osteoarthritic Articular Cartilage (1997), *J. Clin.. Invest*. 99(7): 1534-1545.
Dahlberg, L. et al., Selective Enhancement of Collagenase-Mediated Cleavage of Resident Type II Collagen in Cultured Osteoarthritic Cartilage and Arrest With a Synthetic Inhibitor That Spares Collagenase 1 (Matrix Metalloproteinase 1) (2000), *Arthritis Rheum*., 43(3): 673-682.
Elliott, S, et al. ,The Clinical Potential of Matrix Metalloproteinase Inhibitors in The Rheumatic Disorders (2001), *Drugs and Aging* 18(2): 87-99.
Hanemaauer, et al., MMP-9 Activity in Urine From Patients With Various Tumors, as Measured by a Novel MMP Activity Assay Using Modified Urokinase as a Substrate (1999) . *Annals N.Y. Acad. of Sci*. 878: 141-149.
Huebner, et al., Collagenase 1 and Collagenase 3 Expression in a Guinea Pig Model of Osteoarthritis (1998), *Arthritis Rheum*, 41(5): 877-890.
Kridel S. et al., Substrate Hydrolysis by Matrix Metalloproteinase-9* (2001), *Jour. Biol. Chem*., 276(23): 20572-20578.
Manicourt D-H et al., Serum Levels of Collagenase, Stromelysin-1, and TIMP-1 (1994) *Arthritis & Rheumatism* ,37(12):: 1774-1783.
Mohtai M. et al., Expression of 92-kD Type IV Collagenase/Gelatinase (Gelatinase B) in Osteoarthritic Cartilage and its Induction in Normal Human Articular Cartilage by Interleukin 1 (1993), *J. Clin. Invest*., 92: 179-185.
Naito K. et al. Measurement of Matrix Metalloproteinases (MMPs) and Tissue Inhibitor of Metalloproteinases-1 (TIMP-1) in Patients With Knee Osteoarthritis: Comparison With Generalized Osteoarthritis (1999), *Rheumatology 38*:510-515.
Saltarelli M. et al ,Measurement of Unitary Type II Collagen Neoepitope (uTIINE) Levels in Rheumatoid Arthritis (RA) Patients to Assess Joint Status (1999), *Arthritis Rheum*, 42(9): S249.

(Continued)

*Primary Examiner*—Maher M. Haddad
*Assistant Examiner*—Nora M Rooney
(74) *Attorney, Agent, or Firm*—Laura L. Kiefer

(57) ABSTRACT

Methods for determining matrix metalloproteinase (MMP) activity in biological samples are described. The methods of the invention are useful to assess disease severity or progression, diagnose a particular disease, or develop a profile of MMP activity for inflammatory diseases such as arthritis, or cancer. The methods of the invention involve the use of particular amino acid sequences in substrates to measure the activity in biological samples of MMP's including collagenase 3, stromelysin 1, gelatinase A, gelatinase B and collagenase 1. A diagnostic kit for use in determining the amounts of MMP activities in biological samples is also provided.

9 Claims, 9 Drawing Sheets

OTHER PUBLICATIONS

Smith M. et al., Rapid Identification of Highly Active and Selective Substrates for Stromelysin and Matrilysin Using Bacteriophage Peptide Display Libraries* (1995), *Jour. Biol. Chem.*, 270(12): 6440-6449.
Sopata I. et al. Neutrophil Gelatinase Levels in Plasma and Synovial Fluid of Patients With Rheumatic Diseases (1995), *Rheumatol Int.*, 15:9-14.
Stamenkovic, I. Matrix Metalloproteinases in Tumor Invasion and Metastasis (2000), *Cancer Biology*, 10: 415-433.
Takei I. et al., Matrix Metalloproteinases and Tissue Inhibitors of Metalloproteinases in Joint Fluid of the Patients With Loose Artificial Hip Joints (1999) , J. Biomed. Mater. Res. 45(3): 175-183.
Woodworth T. Urinary Type II Collagen Neoepitope (uTIINE) in Osteoarthritis (OA) Patients is Associated With Disease Severity (1999), *Arthritis and Rheumatism*, 42(9): S258.
Verheijen J. et al., Modified Proenzymes as Artificial Substrates for Proteolytic Enzymes: Colorimetric Assay of Bacterial Collagenase and Matrix Metalloproteinase Activity Using Modified Pro-Urokinase (1997), *Biochem. J.*, 323: 606-609.
Walakovits, L. et al., Detection of Stromelysin and Collagenase in Synovial Fluid From Patients With Rheumatoid Arthritis and Post-traumatic Knee Injury (1992), *Arthritis & Rheumatism*, 35(1): 35-42.
Yoshihara Y. et al., Increased Levels of Stromelysin-1 and Tissue Inhibitor of Metalloproteinases-1 in Sera From Patients With Rheumatoid Arthritis (1995), *Arthritis & Rheumatism*, 38(7): 969-975.
Zucker, S. et al., Critical Appraisal of the Use of Matrix Metalloproteinase Inhibitors in Cancer Treatment (2000) , *Oncogene*, 19(56): 6642-6650.

* cited by examiner

SEQUENCE LISTING

<160> NUMBER OF SEQ ID NOS: 77

<210> SEQ ID NO 1
<211> LENGTH: 8
<212> TYPE: PRT
<213> ORGANISM: Homo sapiens

<400> SEQUENCE: 1

Gly Pro Gln Gly Leu Ala Gly Gln
1 5

<210> SEQ ID NO 2
<211> LENGTH: 7
<212> TYPE: PRT
<213> ORGANISM: Homo sapiens

<400> SEQUENCE: 2

Gly Pro Pro Gly Pro Gln Gly
1 5

<210> SEQ ID NO 3
<211> LENGTH: 7
<212> TYPE: PRT
<213> ORGANISM: Artificial
<220> FEATURE:
<223> OTHER INFORMATION: metalloproteinase substrate

<400> SEQUENCE: 3

Gly Pro Leu Gly Met Arg Gly
1 5

<210> SEQ ID NO 4
<211> LENGTH: 7
<212> TYPE: PRT
<213> ORGANISM: Artificial
<220> FEATURE:
<223> OTHER INFORMATION: metalloproteinase substrate

<400> SEQUENCE: 4

Gly Pro Ile Asn Leu His Gly
1 5

<210> SEQ ID NO 5
<211> LENGTH: 7
<212> TYPE: PRT
<213> ORGANISM: Artificial
<220> FEATURE:
<223> OTHER INFORMATION: metalloproteinase substrate

<400> SEQUENCE: 5

Gly Pro Ser Glu Leu Lys Gly
1 5

<210> SEQ ID NO 6
<211> LENGTH: 6
<212> TYPE: PRT
<213> ORGANISM: Artificial
<220> FEATURE:
<223> OTHER INFORMATION: metalloproteinase substrate

<400> SEQUENCE: 6

Pro His Pro Phe Arg Gly
1 5

-continued

<210> SEQ ID NO 7
<211> LENGTH: 7
<212> TYPE: PRT
<213> ORGANISM: Artificial
<220> FEATURE:
<223> OTHER INFORMATION: metalloproteinase substrate

<400> SEQUENCE: 7

Gly Pro His Pro Phe Arg Gly
1 5

<210> SEQ ID NO 8
<211> LENGTH: 7
<212> TYPE: PRT
<213> ORGANISM: Artificial
<220> FEATURE:
<223> OTHER INFORMATION: metalloproteinase substrate

<400> SEQUENCE: 8

Gly Pro Ser Gly Ile His Val
1 5

<210> SEQ ID NO 9
<211> LENGTH: 8
<212> TYPE: PRT
<213> ORGANISM: Artificial
<220> FEATURE:
<223> OTHER INFORMATION: metalloproteinase substrate

<400> SEQUENCE: 9

Val Thr Pro Tyr Asn Met Arg Gly
1 5

<210> SEQ ID NO 10
<211> LENGTH: 7
<212> TYPE: PRT
<213> ORGANISM: Artificial
<220> FEATURE:
<223> OTHER INFORMATION: metalloproteinase substrate

<400> SEQUENCE: 10

Gly Pro Leu Gln Phe Arg Gly
1 5

<210> SEQ ID NO 11
<211> LENGTH: 7
<212> TYPE: PRT
<213> ORGANISM: Artificial
<220> FEATURE:
<223> OTHER INFORMATION: metalloproteinase substrate

<400> SEQUENCE: 11

Gly Pro Lys Gly Met Arg Gly
1 5

<210> SEQ ID NO 12
<211> LENGTH: 7
<212> TYPE: PRT
<213> ORGANISM: Artificial
<220> FEATURE:
<223> OTHER INFORMATION: metalloproteinase substrate

<400> SEQUENCE: 12

Gly Pro Tyr Gly Met Arg Ala
1 5

<210> SEQ ID NO 13

<211> LENGTH: 7
<212> TYPE: PRT
<213> ORGANISM: Artificial
<220> FEATURE:
<223> OTHER INFORMATION: metalloproteinase substrate

<400> SEQUENCE: 13

Gly Pro Lys Gly Ile Thr Ser
1               5

<210> SEQ ID NO 14
<211> LENGTH: 7
<212> TYPE: PRT
<213> ORGANISM: Artificial
<220> FEATURE:
<223> OTHER INFORMATION: metalloproteinase substrate

<400> SEQUENCE: 14

Gly Pro Arg Pro Phe Arg Gly
1               5

<210> SEQ ID NO 15
<211> LENGTH: 7
<212> TYPE: PRT
<213> ORGANISM: Artificial
<220> FEATURE:
<223> OTHER INFORMATION: metalloproteinase substrate

<400> SEQUENCE: 15

Gly Pro Leu Ser Ile Ser Gly
1               5

<210> SEQ ID NO 16
<211> LENGTH: 7
<212> TYPE: PRT
<213> ORGANISM: Artificial
<220> FEATURE:
<223> OTHER INFORMATION: metalloproteinase substrate

<400> SEQUENCE: 16

Gly Pro Met Ser Tyr Asn Gly
1               5

<210> SEQ ID NO 17
<211> LENGTH: 7
<212> TYPE: PRT
<213> ORGANISM: Artificial
<220> FEATURE:
<223> OTHER INFORMATION: metalloproteinase substrate

<400> SEQUENCE: 17

Gly Pro Leu Ser Ile Gln Asp
1               5

<210> SEQ ID NO 18
<211> LENGTH: 7
<212> TYPE: PRT
<213> ORGANISM: Artificial
<220> FEATURE:
<223> OTHER INFORMATION: metalloproteinase substrate

<400> SEQUENCE: 18

Gly Pro Ser Gly Ile His Leu
1               5

<210> SEQ ID NO 19
<211> LENGTH: 7

-continued

<212> TYPE: PRT
<213> ORGANISM: Artificial
<220> FEATURE:
<223> OTHER INFORMATION: metalloproteinase substrate

<400> SEQUENCE: 19

Gly Pro Val Asn Leu His Gly
1 5

<210> SEQ ID NO 20
<211> LENGTH: 6
<212> TYPE: PRT
<213> ORGANISM: Artificial
<220> FEATURE:
<223> OTHER INFORMATION: metalloproteinase substrate

<400> SEQUENCE: 20

Pro Ser Gly Ile His Leu
1 5

<210> SEQ ID NO 21
<211> LENGTH: 7
<212> TYPE: PRT
<213> ORGANISM: Artificial
<220> FEATURE:
<223> OTHER INFORMATION: metalloproteinase substrate

<400> SEQUENCE: 21

Gly Pro Phe Gly Leu Lys Gly
1 5

<210> SEQ ID NO 22
<211> LENGTH: 7
<212> TYPE: PRT
<213> ORGANISM: Artificial
<220> FEATURE:
<223> OTHER INFORMATION: metalloproteinase substrate

<400> SEQUENCE: 22

Gly Pro His Pro Met Arg Gly
1 5

<210> SEQ ID NO 23
<211> LENGTH: 7
<212> TYPE: PRT
<213> ORGANISM: Artificial
<220> FEATURE:
<223> OTHER INFORMATION: metalloproteinase substrate

<400> SEQUENCE: 23

Gly Pro Leu Gln Met Arg Gly
1 5

<210> SEQ ID NO 24
<211> LENGTH: 12
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(12)
<223> OTHER INFORMATION: Xaa = methylcysteine

<400> SEQUENCE: 24

Asp Glu Gly Pro Met Gly Leu Lys Xaa Tyr Leu Gly
1 5 10

-continued

```
<210> SEQ ID NO 25
<211> LENGTH: 8
<212> TYPE: PRT
<213> ORGANISM: Artificial
<220> FEATURE:
<223> OTHER INFORMATION: metalloproteinase substrate

<400> SEQUENCE: 25

Gly Pro Val Asn Leu His Gly Arg
1               5


<210> SEQ ID NO 26
<211> LENGTH: 12
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(12)
<223> OTHER INFORMATION: Xaa = methylcysteine

<400> SEQUENCE: 26

Val Xaa Pro Lys Gly Ile Thr Ser Xaa Val Phe Arg
1               5                   10


<210> SEQ ID NO 27
<211> LENGTH: 12
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(12)
<223> OTHER INFORMATION: Xaa = methylcysteine

<400> SEQUENCE: 27

Ser Tyr Pro Ser Gly Ile His Leu Xaa Leu Gln Arg
1               5                   10


<210> SEQ ID NO 28
<211> LENGTH: 7
<212> TYPE: PRT
<213> ORGANISM: Artificial
<220> FEATURE:
<223> OTHER INFORMATION: metalloproteinase substrate

<400> SEQUENCE: 28

Gly Pro Leu Gly Leu His Gly
1               5


<210> SEQ ID NO 29
<211> LENGTH: 7
<212> TYPE: PRT
<213> ORGANISM: Artificial
<220> FEATURE:
<223> OTHER INFORMATION: metalloproteinase substrate

<400> SEQUENCE: 29

Gly Pro Leu Gly Phe Arg Gly
1               5


<210> SEQ ID NO 30
<211> LENGTH: 7
<212> TYPE: PRT
<213> ORGANISM: Artificial
<220> FEATURE:
```

```
<223> OTHER INFORMATION: metalloproteinase substrate

<400> SEQUENCE: 30

Gly Pro Leu Gly Phe Arg Val
1               5


<210> SEQ ID NO 31
<211> LENGTH: 7
<212> TYPE: PRT
<213> ORGANISM: Artificial
<220> FEATURE:
<223> OTHER INFORMATION: metalloproteinase substrate

<400> SEQUENCE: 31

Gly Pro Leu Pro Phe His Val
1               5


<210> SEQ ID NO 32
<211> LENGTH: 7
<212> TYPE: PRT
<213> ORGANISM: Artificial
<220> FEATURE:
<223> OTHER INFORMATION: metalloproteinase substrate

<400> SEQUENCE: 32

Gly Pro Ser Pro Phe His Val
1               5


<210> SEQ ID NO 33
<211> LENGTH: 7
<212> TYPE: PRT
<213> ORGANISM: Artificial
<220> FEATURE:
<223> OTHER INFORMATION: metalloproteinase substrate

<400> SEQUENCE: 33

Gly Pro Ser Pro Leu His Gly
1               5


<210> SEQ ID NO 34
<211> LENGTH: 7
<212> TYPE: PRT
<213> ORGANISM: Artificial
<220> FEATURE:
<223> OTHER INFORMATION: metalloproteinase substrate

<400> SEQUENCE: 34

Gly Pro Val Asn Phe Arg Val
1               5


<210> SEQ ID NO 35
<211> LENGTH: 7
<212> TYPE: PRT
<213> ORGANISM: Artificial
<220> FEATURE:
<223> OTHER INFORMATION: metalloproteinase substrate

<400> SEQUENCE: 35

Gly Pro Ala Pro Phe Arg Gly
1               5


<210> SEQ ID NO 36
<211> LENGTH: 7
<212> TYPE: PRT
<213> ORGANISM: Artificial
<220> FEATURE:
<223> OTHER INFORMATION: metalloproteinase substrate
```

<400> SEQUENCE: 36

Gly Pro Ala Pro Phe Arg Val
1 5

<210> SEQ ID NO 37
<211> LENGTH: 7
<212> TYPE: PRT
<213> ORGANISM: Artificial
<220> FEATURE:
<223> OTHER INFORMATION: metalloproteinase substrate

<400> SEQUENCE: 37

Gly Pro Ala Pro Leu His Gly
1 5

<210> SEQ ID NO 38
<211> LENGTH: 7
<212> TYPE: PRT
<213> ORGANISM: Artificial
<220> FEATURE:
<223> OTHER INFORMATION: metalloproteinase substrate

<400> SEQUENCE: 38

Gly Pro Leu Pro Phe Arg Gly
1 5

<210> SEQ ID NO 39
<211> LENGTH: 7
<212> TYPE: PRT
<213> ORGANISM: Artificial
<220> FEATURE:
<223> OTHER INFORMATION: metalloproteinase substrate

<400> SEQUENCE: 39

Gly Pro Leu Pro Phe Arg Val
1 5

<210> SEQ ID NO 40
<211> LENGTH: 7
<212> TYPE: PRT
<213> ORGANISM: Artificial
<220> FEATURE:
<223> OTHER INFORMATION: metalloproteinase substrate

<400> SEQUENCE: 40

Gly Pro Ser Pro Phe Arg Gly
1 5

<210> SEQ ID NO 41
<211> LENGTH: 7
<212> TYPE: PRT
<213> ORGANISM: Artificial
<220> FEATURE:
<223> OTHER INFORMATION: metalloproteinase substrate

<400> SEQUENCE: 41

Gly Pro Ala Pro Leu His Val
1 5

<210> SEQ ID NO 42
<211> LENGTH: 7
<212> TYPE: PRT
<213> ORGANISM: Artificial
<220> FEATURE:
<223> OTHER INFORMATION: metalloproteinase substrate

<400> SEQUENCE: 42

Gly Pro Leu Gly Leu His Val
1 5

<210> SEQ ID NO 43
<211> LENGTH: 7
<212> TYPE: PRT
<213> ORGANISM: Artificial
<220> FEATURE:
<223> OTHER INFORMATION: metalloproteinase substrate

<400> SEQUENCE: 43

Gly Pro Leu Pro Leu His Gly
1 5

<210> SEQ ID NO 44
<211> LENGTH: 8
<212> TYPE: PRT
<213> ORGANISM: Artificial
<220> FEATURE:
<223> OTHER INFORMATION: metalloproteinase substrate

<400> SEQUENCE: 44

Gly Pro Leu Gly Met Arg Gly Cys
1 5

<210> SEQ ID NO 45
<211> LENGTH: 7
<212> TYPE: PRT
<213> ORGANISM: Artificial
<220> FEATURE:
<223> OTHER INFORMATION: metalloproteinase substrate

<400> SEQUENCE: 45

Gly Pro Leu Met Arg Gly Cys
1 5

<210> SEQ ID NO 46
<211> LENGTH: 8
<212> TYPE: PRT
<213> ORGANISM: Artificial
<220> FEATURE:
<223> OTHER INFORMATION: metalloproteinase substrate

<400> SEQUENCE: 46

Gly Pro Val Asn Leu His Gly Cys
1 5

<210> SEQ ID NO 47
<211> LENGTH: 8
<212> TYPE: PRT
<213> ORGANISM: Artificial
<220> FEATURE:
<223> OTHER INFORMATION: metalloproteinase substrate

<400> SEQUENCE: 47

Gly Pro His Pro Phe Arg Gly Cys
1 5

<210> SEQ ID NO 48
<211> LENGTH: 6
<212> TYPE: PRT
<213> ORGANISM: Artificial
<220> FEATURE:
<223> OTHER INFORMATION: metalloproteinase substrate

<400> SEQUENCE: 48

Pro Ile Asn Leu His Gly
1 5

<210> SEQ ID NO 49
<211> LENGTH: 7
<212> TYPE: PRT
<213> ORGANISM: Artificial
<220> FEATURE:
<223> OTHER INFORMATION: metalloproteinase substrate

<400> SEQUENCE: 49

Gly Pro Leu Ser Phe Gln Gly
1 5

<210> SEQ ID NO 50
<211> LENGTH: 6
<212> TYPE: PRT
<213> ORGANISM: Artificial
<220> FEATURE:
<223> OTHER INFORMATION: metalloproteinase substrate

<400> SEQUENCE: 50

Pro Leu Gly Met Arg Gly
1 5

<210> SEQ ID NO 51
<211> LENGTH: 6
<212> TYPE: PRT
<213> ORGANISM: Artificial
<220> FEATURE:
<223> OTHER INFORMATION: metalloproteinase substrate

<400> SEQUENCE: 51

Pro Ser Gly Ile His Leu
1 5

<210> SEQ ID NO 52
<211> LENGTH: 9
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(9)
<223> OTHER INFORMATION: Xaa = methylcysteine

<400> SEQUENCE: 52

Gly Pro Val Asn Leu His Gly Arg Xaa
1 5

<210> SEQ ID NO 53
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 53

Gly Pro Val Asn Leu His Gly Xaa
1 5

<210> SEQ ID NO 54

-continued

<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 54

Gly Pro Leu Gly Leu His Gly Xaa
1 5

<210> SEQ ID NO 55
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 55

Gly Pro Leu Gly Phe Arg Gly Xaa
1 5

<210> SEQ ID NO 56
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 56

Gly Pro Leu Gly Phe Arg Val Xaa
1 5

<210> SEQ ID NO 57
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 57

Gly Pro Leu Pro Phe His Val Xaa
1 5

<210> SEQ ID NO 58
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 58

```
Gly Pro Ser Pro Phe His Val Xaa
1               5


<210> SEQ ID NO 59
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 59

Gly Pro Ser Pro Leu His Gly Xaa
1               5


<210> SEQ ID NO 60
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 60

Gly Pro Val Asn Phe Arg Val Xaa
1               5


<210> SEQ ID NO 61
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 61

Gly Pro Ala Pro Phe Arg Gly Xaa
1               5


<210> SEQ ID NO 62
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 62

Gly Pro Ala Pro Phe Arg Val Xaa
1               5


<210> SEQ ID NO 63
<211> LENGTH: 8
<212> TYPE: PRT
<213> ORGANISM: Artificial
<220> FEATURE:
<223> OTHER INFORMATION: metalloproteinase substrate
```

```
<220> FEATURE:
<221> NAME/KEY: MISC_FEATURE
<222> LOCATION: (1)..(8)
<223> OTHER INFORMATION: Xaa = methylcysteine

<400> SEQUENCE: 63

Gly Pro Ala Pro Leu His Gly Xaa
1               5


<210> SEQ ID NO 64
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 64

Gly Pro Leu Pro Phe Arg Gly Xaa
1               5


<210> SEQ ID NO 65
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 65

Gly Pro Leu Pro Phe Arg Val Xaa
1               5


<210> SEQ ID NO 66
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 66

Gly Pro Ser Pro Phe Arg Gly Xaa
1               5


<210> SEQ ID NO 67
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 67

Gly Pro Ala Pro Leu His Val Xaa
1               5
```

```
<210> SEQ ID NO 68
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 68

Gly Pro Leu Gly Leu His Val Xaa
1               5


<210> SEQ ID NO 69
<211> LENGTH: 8
<212> TYPE: PRT
<213> ORGANISM: Artificial
<220> FEATURE:
<223> OTHER INFORMATION: metalloproteinase substrate
<220> FEATURE:
<221> NAME/KEY: MISC_FEATURE
<222> LOCATION: (1)..(8)
<223> OTHER INFORMATION: Xaa = methylcysteine

<400> SEQUENCE: 69

Gly Pro Leu Pro Leu His Gly Xaa
1               5


<210> SEQ ID NO 70
<211> LENGTH: 10
<212> TYPE: PRT
<213> ORGANISM: Homo sapiens

<400> SEQUENCE: 70

Pro Lys Gly Val Phe Ser Gly Leu Arg Asn
1               5                   10


<210> SEQ ID NO 71
<211> LENGTH: 11
<212> TYPE: PRT
<213> ORGANISM: Homo sapiens

<400> SEQUENCE: 71

His Lys Tyr Ala Leu Val Leu Val Asn Asn Lys
1               5                   10


<210> SEQ ID NO 72
<211> LENGTH: 7
<212> TYPE: PRT
<213> ORGANISM: Artificial
<220> FEATURE:
<223> OTHER INFORMATION: motif for collagen cleavage site
<220> FEATURE:
<221> NAME/KEY: MISC_FEATURE
<222> LOCATION: (1)..(7)
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 72

Ser Xaa Gly Pro Xaa Gly Ile
1               5
```

-continued

```
<210> SEQ ID NO 73
<211> LENGTH: 10
<212> TYPE: PRT
<213> ORGANISM: Homo sapiens

<400> SEQUENCE: 73

Phe Pro Gly Ser Pro Gly Pro Met Gly Ile
1               5                   10


<210> SEQ ID NO 74
<211> LENGTH: 16
<212> TYPE: PRT
<213> ORGANISM: Artificial
<220> FEATURE:
<223> OTHER INFORMATION: motif for collagen cleavage site
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(8)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 74

Xaa Ser Gly Ala Xaa Xaa Xaa Xaa Gly Ala Pro Gly Ile Phe Xaa Leu
1               5                   10                  15


<210> SEQ ID NO 75
<211> LENGTH: 16
<212> TYPE: PRT
<213> ORGANISM: Homo sapiens

<400> SEQUENCE: 75

Ile Ser Gly Ala Pro Gly Asp Lys Gly Ala Pro Gly Ile Phe Gly Leu
1               5                   10                  15


<210> SEQ ID NO 76
<211> LENGTH: 19
<212> TYPE: PRT
<213> ORGANISM: Homo sapiens

<400> SEQUENCE: 76

Pro Ser Asn Ile Ser Gly Ala Pro Gly Asp Lys Gly Ala Pro Gly Ile
1               5                   10                  15

Gly Phe Leu


<210> SEQ ID NO 77
<211> LENGTH: 11
<212> TYPE: PRT
<213> ORGANISM: Artificial
<220> FEATURE:
<223> OTHER INFORMATION: hypothetical metalloproteinase substrate

<400> SEQUENCE: 77

Cys Ala Asp Glu Phe Gly His Ile Lys Leu Met
1               5                   10
```

ASSAYS FOR MEASURING MATRIX METALLOPROTEINASE ACTIVITIES

RELATED APPLICATION

This application claims priority under 35 U.S.C. §119(e) to U.S. Provisional Application 60/384,135, filed May 31, 2002, which is herein incorporated by reference in its entirety.

FIELD OF THE INVENTION

This application relates to assays for measuring matrix metalloproteinase (MMP) activities in biological samples and novel substrates for use in such assays. In particular, peptide substrates having increased specificity for collagenase 3 are disclosed, which may be detected via an attached label or through the use of neo-epitope antibodies specific for the cleavage products of such peptide substrates. Various means for increasing the sensitivity of the MMP assays are also reported, including the use of inhibitors and activators of MMP enzymes to increase the sensitivity of substrate/enzyme reactions. Multiple enzyme/multiple substrate assays are also provided whereby standard rates of response for particular enzyme/substrate pairs are compared to the rates of response for a mixed enzyme sample in order to allow for the calculation of the concentrations of particular enzymes in a mixed sample. Assays for detecting and quantifying MMP activities find use in diagnosing diseases such as cancer and arthritis.

BACKGROUND OF THE INVENTION

Matrix metalloproteinases (MMPs) belong to the metzincin superfamily of zinc peptidases and include enzymes such as collagenase 3 (MMP 13), collagenase 1 (MMP 1), stromelysin 1 (MMP 3), gelatinase A (MMP 2), and gelatinase B (MMP 9) (Bode et al. (1996) Adv Exp Med Biol 389:1-11). MMPs are able to cleave components of the cartilage matrix. Accordingly, aberrant regulation of MMPs has been implicated in the collagen breakdown that occurs during certain diseases, such as rheumatoid arthritis and osteoarthritis (Shaw et al. (2000) Expert Opin. Investig. Drugs 9: 1469-78).

For instance, gelatinase levels have been shown to be significantly higher in the plasma of patients with rheumatoid arthritis (RA) and patients with RA complicated by amyloidosis or vasculitis as compared to healthy controls (Sopata et al. (1995) Rheumatol. Int. 15: 9-14). Expression of gelatinase B in fibrillated cartilage has been described as a useful marker of progressive articular cartilage degradation in osteoarthritis (Mohtai et al. (1993) J. Clin. Invest. 92: 179-85). Yoshihara and colleagues found increased levels of stromelysin-1 (MMP3) and a tissue inhibitor of metalloproteinases 1 (TIMP-1) in serum of rheumatoid arthritis patients as compared to osteoarthritis patients and healthy controls (Yoshihara et al. (1995) Arthritis Rheum. 38(7): 969-75; see also Garnero et al. (2002) Arthritis Rheum. 46(1): 21-30, and Walakovitz et al. (1992) Arthritis Rheum. 35(1): 35-42). In turn, plasma levels of MMP3 and TIMP1 have been shown to be significantly higher in osteoarthritis patients as compared to healthy subjects (Naito et al. (1999) Rheum. 38(6): 510-5). It has been suggested that MMP13 (collagenase 3) participates in tissue destruction in rheumatoid synovium and joint fluid (Lindy et al. (1997) Arthritis Rheum. 40: 1391-99), however the lack of an appropriate assay for MMP13 has been noted recently (Takei et al. (1999) J. Biomed. Mater. Res. 45: 175-83).

Once collagen is lost, it is rarely replaced. Therefore, the prevention of collagen degradation is an important aspect for the design of an effective treatment for rheumatoid arthritis and osteoarthritis, and research continues for effective inhibitors in view of this great unmet medical need (Elliott & Cawston (2001) Drugs Aging 18(2): 87-99). Early detection of the breakdown of collagen components would be a valuable first step in permitting the prevention of collagen degradation, by permitting the identification of patients in the early stages of arthritic disease.

In addition, MMPs are necessary for cancer progression, metastasis, and angiogenesis (new blood vessel formation). Because MMPs are able to degrade extracellular matrix (ECM) proteins, they are thought to facilitate tumor development by breaking down tissue barriers to invasion, thereby creating a path for tumor cells to colonize host tissues (Stamenkovic (2000) Semin. Cancer Biol. 10(6): 415-33). Numerous in vitro studies involving the use of inhibitors of MMP enzymes in reconstituted or cell-derived basement membrane systems support this view (Albini et al. (1991) J. Natl. Cancer Inst. 83: 775-79; DeClerk et al. (1991) Cancer Res. 51: 2151-57; DeClerk et al. (1992) Cancer Res. 52: 701-08; Khokha et al. (1992) J. Natl. Cancer Inst. 84: 1017-22). Recent evidence suggests that MMPs in the vicinity of tumors are produced by stromal cells rather than the tumor cells themselves, whereby the cancer cells induce stromal cells to synthesize MMPs using extracellular matrix metalloproteinase inducer (EMMPRIN) and cytokine stimulatory mechanisms in order to facilitate their invasion of tissues and local micrometastasis (Zucker et al. (2000) Oncogene 19(56): 6642-50). Thus, given that MMPs are required for the early steps of cancer progression and metastasis, detecting aberrant MMP activity can be an early indicator for the spread of invasive cancers.

For instance, Gohji and colleagues found that the mean serum level of MMP2 in prostate cancer patients was significantly higher in prostate cancer patients as compared to healthy controls and patients with benign prostatic hyperplasia (Gohji et al. (1998) Int. J. Cancer 78(3): 392-3). In another study, Hayasaka and colleagues showed that MMP9 levels were significantly higher in patients with hepatocellular carcinoma (HCC) as compared with healthy controls, patients with chronic hepatitis and patients with liver cirrhosis (Hayasaka et al. (1996) Hepatol. 24(5): 1058-62). Similarly, levels of MMP2 were found to be significantly elevated in the sera of Stage IV lung cancer patients as compared to normal sera (Garbisa et al. (1992) Cancer Res. 52(16): 4548-9; see also Hrabec et al. (2002) J. Cancer Res. Clin. Oncol. 128(4): 197-204). More recently, overexpression of stromelysin 3 (MMP11) was identified as a useful prognostic marker for the invasive potential of non-small cell lung cancer (Delebecq et al. (2000) Clin. Cancer Res. 6(3): 1086-92).

While elevated levels of particular MMP enzymes have been shown to be associated with particular types of cancer or inflammatory diseases, other groups have reported increases in particular MMPs over others in certain disorders. For instance, Riedel and colleagues reported a significant increase in MMP9 serum concentrations of patients with advanced stage head and neck squamous cell carcinomas as compared to patients with early stage cancer. However, no significant difference in MMP2 serum levels was observed (Riedel et al. (2000) Anticancer Res. 20(5A): 3045-9). In contrast, both MMP2 and MMP9 levels were found to be significantly higher in primary tumors from patients with either synchronous or metachronous metastases as compared to patients who were disease-free following radical nephrectomy (Slaton et al. (2001) Am. J. Pathol. 158(2): 735-43).

Thus, the level of particular MMPs may vary depending on the type and/or stage of cancer, therefore specific diagnostics tests that are capable of distinguishing between various MMPs would be valuable in diagnosing different types of cancer. Furthermore, given the lack of sensitivity and specificity of substrates used in the prior assays, more sensitive substrates would permit an accurate evaluation of which MMPs show elevated expression in particular patient populations.

Assays to measure (MMP) activity in biological fluids have been described elsewhere (Verheijen et al. Biochem J. (1997) May 1; 323(Pt 3): 603-9; Beekman et al. (1999) Ann NY Acad Sci. June 30; 878: 150-8; Beekman et al. (1997) FEBS Lett. December 1; 418(3): 305-9; Beekman et al. (1996) FEBS Lett 390: 221-5) and commercially available kits exist (Amersham Biotrak™ ELISA system, RPN2632), but none are specific or sensitive enough or designed to measure MMP activity directly in bodily fluids and thus, are not of clinical benefit to the patient. Obtaining a profile of MMP activity is important because it may serve as a predictor of disease progression or even a diagnostic tool in diseases such as osteoarthritis (OA), rheumatoid arthritis (RA) and cancer. Thus, research to find informative markers that can serve as dosimeters of these diseases continues, as there are currently no robust and reliable commercial tests.

For instance, a colorimetric assay was developed (Verheijen et al., 1997) that relies on cleavage of a sequence preferred by MMPs within a full length protein. This colorimetric procedure was used for a MMP-9 assay that measures gelatinase B activity in urine (Hanemaaijer et al. (1999) Ann. N.Y. Acad. Sci. 878: 141-9). This technique may not, however, be sensitive enough to measure collagenase 3 levels in biological fluids where picomolar amounts are present.

Preliminary data with fluorescent peptide substrates to measure MMP activity in synovial fluid have been reported and are sensitive, but the peptides did not have a proper sequence so as to confer enough selectivity to permit an accurate measurement of collagenase 3 activity in biological samples such as synovial fluid, plasma and urine. MMPs such as the gelatinases, collagenase 1 and stromelysin are present in abundant quantities, but the currently available collagenase 3 substrate is only 8, 3, and 60 fold selective over gelatinase B, gelatinase A, and stromelysin (Beekman et al, 1999), respectively. Unfortunately, stromelysin is an enzyme that is prevalent in synovial fluid and blood plasma during disease states such as rheumatoid arthritis and is therefore likely to contribute to the measurable activity when non-specific substrates are employed (Yoshihara et al. (1995)).

Kits are commercially available from Amersham that measure MMP activities using a calorimetric assay in a 96-well plate format. Semi-specific antibodies are used to pull a given MMP out of the biological fluid and then activity is measured via addition of a substrate that produces a color upon cleavage. Several problems exist with these kits. First, since the antibodies are not completely specific, a single enzyme assay may in fact measure a composite of MMP activities. Second, the assay is colorimetric and is not very sensitive. For instance, the Amersham kit is only capable of detecting nanomolar levels of MMP enzyme, as compared to the novel substrates disclosed herein, which detect picomolar quantities of collagenase 3 activity. Finally, for at least the Amerhsam collagenase 3 kit, the signal detected is independent of antibody addition, suggesting that the kit does not in fact accurately measure collagenase 3 levels.

Another way in which to assess MMP activity is with neo-epitope antibodies to the cleavage products of substrates. This technique has been used to assess disease activity in patients with rheumatoid and osteoarthritis, where efforts have focused on the proteases that degrade type II collagen, the principle collagen of the joint. Poole and coworkers discovered that the major cleavage point of type II collagen by the matrix metalloproteases 1 and 13 (collagenase 1 and 3) occurs at the sequence GPQGLAGQ (SEQ ID NO: 1). Using neo-epitope Abs to that sequence, they detected processed collagen fragments in synovial fluid from rheumatoid or osteoarthritic patients (Billinghurst et al. (1997) J. Clin. Invest. 99: 1534-1545; Dahlberg et al. (2000) Arthritis Rheum. March; 43(3): 673-82). These neoepitope antibodies are not commercially available. Moreover, the sequence detected by this antibody, GPQG-NH2, can arise from cleavages by other MMP enzymes.

Another neo-epitope antibody to the sequence at the 3/4 collagen I or II cleavage site has been created by Pfizer (Huebner et al. (1999) Trans. Orthop. Res. Soc. 25: 198). This antibody, 9A4, recognizes the sequence GPP(OH)GPQG—COOH (SEQ ID NO: 2) (Huebner et al. (1998) Arthritis Rheum. 41: 877-890). Together with an upstream anti-collagen II specific antibody, collagen fragments are detected in urine (the urinary type II collagen neo-epitope assay or uTIINE) (Saltarelli et al. (1999) Arthritis Rheum. 42(9): 1071). The urinary TIINE activity has been shown to correlate with OA disease activity (Woodworth et al. (1999) Arthritis Rheum. 42(9): 1125), thereby demonstrating the importance of collagenase activity in the osteoarthritis disease process. These assays, however, are not commercially available and do not discern the particular collagenase or relative contribution of the various collagenases in different arthritides.

Recently, a role for collagenase 3, gelatinase A and gelatinase B in the processing of protein substrates has been discovered by utilizing substrate mapping with phage display (Deng et al. (2000) J. Biol. Chem. 275: 31422-7; Kridel et al. (2001) J Biol Chem. 276(23): 20572-8; Chen et al., J Biol Chem (IN PRESS)). Substrate mapping with phage display has also been performed with stromelysin 1, although the information was not used to design very specific substrates, nor were physiological substrates found for this enzyme (Smith et al. (1995) J Biol Chem. March 24; 270(12): 6440-9). In the case of collagenase 3, peptide substrates are cleaved that display sequence homology with type IV collagen, biglycan, and TGF-beta-3 (Deng et al, 2000).

Using the previous phage display data as a starting point, the present inventors were successful in obtaining many substrate sequences showing enhanced selectivity for collagenase 3 over the other matrix metalloproteases. In the process of identifying these substrates, the inventors identified several structure/function relationships useful for the design of substrates having specificity and selectivity for collagenase 3. Further, in the process of designing assays for the use of these substrates, the present inventors identified several improvements over existing assays that would increase the selectivity and sensitivity of MMP assays in general. These novel substrates for collagenase 3 and improved MMP assays are useful tools for measuring MMP activity in disease states where levels/activities are discordant in comparison with healthy subjects.

SUMMARY OF INVENTION

The invention encompasses novel substrates for MMP enzymes, including novel peptide substrates showing increased selectivity for collagenase 3 over other MMPs such as stromelysin 1, collagenase 1 and gelatinases A and B.

Labeled substrates are used in novel methods of detecting and measuring MMPs in mixed samples, for instance biological samples from patients having cancer or a variety of inflammatory disorders where levels of MMPs may be elevated. Neo-epitope antibodies that bind to cleavage products of natural MMP substrates or cleavage products of the substrates disclosed herein are also described for use in the disclosed methods.

Methods of measuring MMPs according to the invention include, among others, measuring cleavage of one or more of the peptide substrates disclosed herein. Improved MMP assays are also disclosed that include steps for activating MMP activity or inhibiting the activity of particular MMPs in order to enhance sensitivity and selectivity for a target MMP of interest. Also envisioned are multiple enzyme/multiple substrate formats whereby the concentration of two or more enzymes in a mixed sample may be determined by solving simultaneous linear equations based on observed reaction rates. Diagnostic kits incorporating one or more of the substrates disclosed herein are also included, as are kits that are formulated to facilitate one or more of the novel methods described.

DETAILED DESCRIPTION OF THE INVENTION

Figure 1:
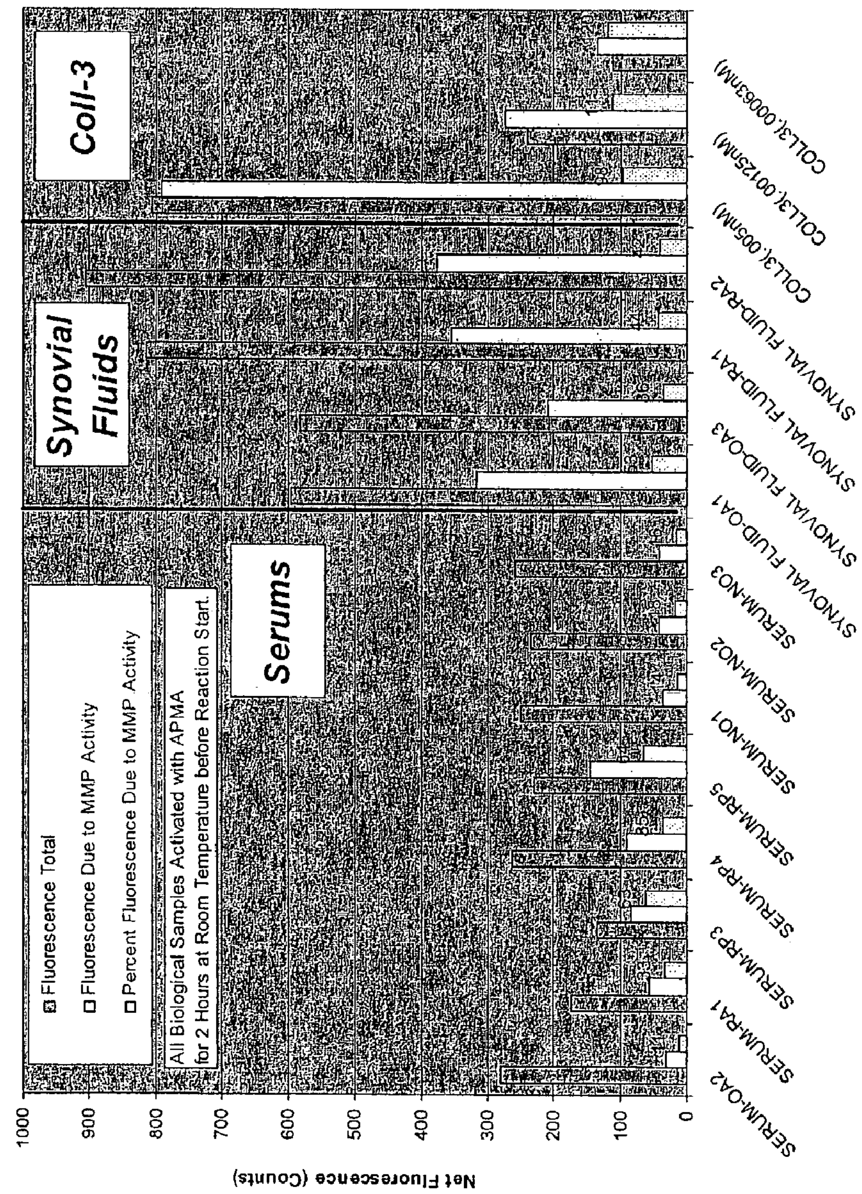
FIG. 1. Graph showing net fluorescence due to MMP activity for serum and synovial fluids from osteoarthritis (OA), rheumatoid arthritis (RA) and Relapsing Polychondritis (RP) patients, as measured by fluorescence substrate 1 in the presence of 1:250 gelatin.

The invention provides, among other embodiments, novel substrates for MMP enzymes such as collagenase 3. Such substrates are generally peptides comprising sequences that are recognized and cleaved by collagenase 3. Substrates may be labeled or unlabeled, and may comprise either natural, unnatural (rare) or synthetic amino acids. Peptides are described that demonstrate increased selectivity and/or specificity for collagenase 3 over peptide substrates of the prior art, and may detect collagenase 3 at or below picomolar levels. For instance, the substrates disclosed herein detect collagenase 3 across the entire range of about 100 to about 5000 pg/ml. The substrates disclosed herein may be used to detect collagenase 3 at levels of about 10 or less pg/ml, 15, 20, 25, 35, 50, 75, 100, 150, 200, 250, 300, 500, etc. to 5000 pg/ml.

"Specificity" in the context of this application means the fractional turnover of a substrate per unit of time (units $s^{-1}$ $M^{-1}$), or in other words, how quickly a unit of an enzyme converts a substrate. "Selectivity" is the ratio of specificity of two enzymes for a particular substrate, or in other words, the speed of a first enzyme divided by the speed of a second enzyme against the same substrate.

In general, peptide substrates having the selectivities and specificities described herein have a consensus sequence of the formula P4-P3-P2-P1-P1'-P2'-P3'-P4', wherein a typical sequence comprises:

(a) a glycine residue at position P4;

(b) a proline residue at position P3;

(c) an amino acid residue at position P2 that is selected from the group consisting of leucine, serine, valine, alanine, methionine, histidine, arginine, lysine, tyrosine and isoleucine;

(d) an amino acid residue at position P1 that is selected from the group consisting of glycine, proline, serine, asparagine, glutamine and glutamate;

(e) an amino acid residue at position P1' that is selected from the group consisting of leucine, phenylalanine, methionine, isoleucine, tyrosine and methionine;

(f) an amino acid residue at position P2' that is selected from the group consisting of histidine, arginine, serine, asparagine, glutamine, lysine and threonine;

(g) an amino acid residue at position P3' that is selected from the group consisting of glycine, valine, alanine, serine, leucine and aspartate; and (h) a natural or synthetic amino acid residue at the P4' position that can attach to a detectable label.

Peptides having longer sequences than the consensus sequence shown above are also encompassed as illustrated herein. It may also be possible to substitute the various amino acids listed above with other natural, unnatural and synthetic amino acids have similar properties. For instance, the inventors envision that appropriate amino acids at position P2 may be aliphatic, hydrophobic and/or positively charged. Similarly, appropriate amino acid residues for position P1 may be aliphatic and/or hydrogen bonding. Appropriate amino acids for position P1' may be aliphatic and/or hydrophobic. Appropriate amino acids for position P2' may be hydrogen bonding, and those for position P3' may be aliphatic, hydrophobic or hydrogen bonding. Other amino acids may also be substituted for the positions described above so long as such peptides are capable of detecting collagenase 3 across the entire range of concentrations described above, i.e., from about 100 to about 5000 pg/ml.

A natural or synthetic amino acid residue is typically included at position P4' that can attach to a detectable label, for instance, a cysteine with the sulfhydryl group blocked.

However, the peptide substrates disclosed herein need not be attached to labels, particularly when they are used in embodiments permitting neo-epitope antibody detection of substrate cleavage products. It will also be possible to include internal amino acids capable of attaching to a detectable label, such as those illustrated herein among others. It should be understood that "attached" encompasses both "incorporated" labels (whereby a labeled amino acid is incorporated into the peptide sequence during synthesis) and "conjugated" labels (which are attached to peptide following synthesis). It may also be possible to replace a side chain of an amino acid, thereby changing the nature of the labeled amino acid in the process of the labeling reaction.

The specific peptide substrates reported herein have improved selectivity for collagenase 3 over at least one competing matrix metalloproteinase (MMP) enzyme. Competing MMP enzymes include gelatinase A, gelatinase B, collagenase 1 and stromelysin 1, among others. For instance, the invention encompasses substrates comprising a peptide sequence selected from the group consisting of: GPLGMRG (SEQ ID NO: 3), GPINLHG (SEQ ID NO: 4), GPSELKG (SEQ ID NO: 5), PHPFRG (SEQ ID NO: 6), GPHPFRG (SEQ ID NO: 7), GPSGIHV (SEQ ID NO: 8), VTPYNMRG (SEQ ID NO: 9), GPLQFRG (SEQ ID NO: 10), GPKGMRG (SEQ ID NO: 11), GPYGMRA (SEQ ID NO: 12), GPKGITS (SEQ ID NO: 13), GPRPFRG (SEQ ID NO: 14), GPLSISG (SEQ ID NO: 15), GPMSYNG (SEQ ID NO: 16), GPLSIQD (SEQ ID NO: 17), GPSGIHL (SEQ ID NO: 18), GPVNLHG (SEQ ID NO: 19), PSGIHL (SEQ ID NO: 20), GPFGLKG (SEQ ID NO: 21), GPHPMRG (SEQ ID NO: 22), GPLQMRG (SEQ ID NO: 23), DEGPMGLKC(Me)YLG (SEQ ID NO: 24), GPVNLHGR (SEQ ID NO: 25), VC(Me) PKGITSXVFR (SEQ ID NO: 26), SYPSGIHLC(Me)LQR (SEQ ID NO: 27), GPLGLHG (SEQ ID NO: 28), GPLGFRG (SEQ ID NO: 29), GPLGFRV (SEQ ID NO: 30), GPLPFHV (SEQ ID NO: 31), GPSPFHV (SEQ ID NO: 32), GPSPLHG (SEQ ID NO: 33), GPVNFRV (SEQ ID NO: 34), GPAPFRG (SEQ ID NO: 35), GPAPFRV (SEQ ID NO: 36), GPAPLHG (SEQ ID NO: 37), GPLPFRG (SEQ ID NO: 38), GPLPFRV (SEQ ID NO: 39), GPSPFRG (SEQ ID NO: 40), GPAPLHV (SEQ ID NO: 41), GPLGLHV (SEQ ID NO: 42), and GPLPLHG (SEQ ID NO: 43). When the substrates of the invention are labeled, they may be attached to any suitable label, including chemical, fluorescent and protein labels. Some possible labels include Dnp, dinitrophenyl; Dab, Dabcyl; Flu, Fluorescein, DMC, dimethyl amino coumarin; AMCA, 6-((7-amino-4-methylcoumarin-3-acetyl)amino) hexanoic acid; EDANS, 5-((2-aminoethyl) amino)naphthalene-1-sulfonic acid; NBD, 6-(N-(7-nitrobenz-2-oxa-1,3-diazol-4-yl)amino)hexanoic acid, among others.

Methods of attaching labels to amino acids and other materials, and methods of using labels to detect and monitor enzyme reactions and conversion of substrates, are well known in the art. For instance, The Handbook of Fluorescent Probes and Research Products published and frequently updated by Molecular Probes, Inc. provides a comprehensive overview of appropriate labels for particular methodologies, including compounds for labeling peptides. The eighth edition of this handbook, recently available online and also available as a CDrom, is herein incorporated by reference in its entirety. A fluorescent label may be attached to one end of the peptide or to an amino acid on one side of the cleavage site and a quencher molecule to the other end of the peptide or to an amino acid on the other side of the cleavage site, for instance for use in fluorescence resonance energy transfer embodiments. Methods of making such peptides are disclosed in U.S. Pat. No. 6,037,137, which is herein incorporated by reference.

Peptide substrates described herein may be used in methods for detecting MMP enzymes in samples. For instance, a method for detecting the presence of collagenase 3 in a sample may comprise (a) contacting the sample with at least one peptide substrate as described herein, and (b) detecting cleavage of said substrate, wherein the level of cleavage of said substrate may be correlated to the level of collagenase 3 in said sample. Some embodiments included herein comprise adding at least one further substrate for one or more competing MMPs at step (a). A "further" substrate may be a natural substrate for the competing MMP or an internal peptide sequence of said natural substrate. "Natural" substrates refer to substrates for MMP enzymes encountered in nature, such as type 1 collagen, type II collagen, fibronectin, and gelatin, for instance. Such "further" substrates may also be attached to a detectable label according to the methods described herein.

Other embodiments comprise adding at least one inhibitor for a competing MMP at step (a). Appropriate inhibitors include transition state analogues based on the sequence of said one or more peptide substrate(s) described herein. Such analogs are produced by adding a phosphinic or phosphinate group anywhere in the peptide sequence according to well known methods (Jens-Buchardt et al. (2000) J. Comb. Chem 2: 624-38; Jens-Buchardt et al. (1999) Chem Eur. J. 5: 2877-2884; Vassiliou et al. (1999) J. Med.Chem. 42: 2610-20; Reiter et al. (1999) Bioorg. Med. Chem. Lett. 9: 127-132 Goulet et al. (1994) Bioorg. Med. Chem. Lett. 4: 1221-4; Yiotakis et al. (1994) Biochem. J. 303: 323-27; and Caldwell et al (1996) Bioorg. Med. Chem. Lett 6: 323-328). Appropriate inhibitors also include natural or synthetic substrates for competing MMPs or internal peptide sequences thereof, in that substrates having increased selectivity for a competing MMP will occupy its activity, thereby increasing sensitivity of the first substrate for the target MMP, i.e., collagenase 3.

Other embodiments include adding at least one activator of MMP activity at step (a). Appropriate activators include amino phenyl mercuric acetate (APMA), proteolytic enzymes of the furin family and membrane bound MMPs (MT-MMPs), or any other MMP activating substance.

In embodiments where substrates are attached to a fluorescent label, cleavage of the substrate may be detected by measuring a change in fluorescence over time using techniques and apparatuses known in the art. Where the label is a calorimetric label, cleavage of the substrate may be detected by measuring a change in absorbence and/or high pressure liquid chromatography (HPLC) profile over time. Where the label is a radioactive label, cleavage of the substrate may be detected by measuring a change in radioactivity over time. And where the label is a luminescent label, cleavage of the substrate may be detected by measuring a change in luminescence over time. Again, methods of making labeled peptides and quantifying cleavage of peptides using such labeled peptides are known in the art, such as provided in The Handbook of Fluorescent Probes and Research Products published and frequently updated by Molecular Probes, Inc. and U.S. Pat. No. 6,037,137, which are both herein incorporated by reference in their entireties.

One embodiment, among others reported herein, is an improved method for detecting the presence of a non-gelatinase MMP enzyme in a sample comprising:

a) contacting said sample with a substrate that is cleaved by said MMP and an effective amount of gelatin to inhibit gelatinases in said sample, and b) detecting cleavage of said substrate, wherein the level of cleavage of said substrate may be correlated to the level of non-gelatinase MMP in said sample. A non-gelatinase MMP, for instance, would be collagenase 3, but not gelatinase A or gelatinase B. This method is based on the novel discovery reported herein that including gelatin in assays for non-gelatinase MMP enzymes can improve selectivity of substrates for non-gelatinase enzymes.

Also encompassed is an improved method for detecting the presence of a non-gelatinase MMP enzyme in a sample comprising:

a) contacting said sample with a substrate that is cleaved by said MMP and an effective amount of type II collagen to inhibit gelatinases in said sample, and b) detecting cleavage of said substrate, wherein the level of cleavage of said substrate may be correlated to the level of non-gelatinase MMP in said sample. This method is based on the novel discovery reported herein that including type II collagen in assays for non-gelatinase MMP enzymes can improve selectivity of substrates for non-gelatinase enzymes, such as collagenase 3, among others.

The methods reported herein are applicable to measuring activities of MMPs in any sample. For example, the methods reported herein could be used to measure the purity, stability or remaining activity of MMP enzyme preparations, for instance after a period in storage in order to monitor any enzyme breakdown. The assays described herein may also be used to measure MMP activities in biological fluids, for instance for the purpose of diagnosing disease or for evaluating the involvement of particular MMP enzymes in different types of diseases. Such diseases would include, among others, any inflammatory disorder or disease, autoimmune disease, multiple sclerosis, diabetes, cancer, Alzheimer's Disease, stroke, spinal cord injury, central nervous system diseases, rheumatoid arthritis, osteoarthritis, Crohn's disease, glomerular nephritis and restenosis macular degeneration, periodontal disease, chronic obstructive pulmonary disease, asthma, osteoporosis or any disease or disorder of the bones or joints. Appropriate biological fluids for testing will depend on the disease or disorder, but would include blood, serum, synovial fluid, urine, saliva, cerebral/spinal fluid and bronchial alveolar lavage fluid, to name just a few.

The invention also includes isolated neo-epitope antibodies specific for the N or C terminal cleavage products of the collagenase 3 substrates described herein following digestion by collagenase 3. Such antibodies include monoclonals, polyclonals, and chimeric and humanized antibodies constructed using the variable binding domains of the neo-epitope antibodies described herein, as well as antibody fragments, such as Fv or $F(ab)_2$ antibody fragments. Also included are neo-epitope antibodies that recognize cleavage products type IV collagen or biglycan following digestion with collagenase 3, gelatinase A or gelatinase B.

Another embodiment is a diagnostic kit for calculating the amount of collagenase 3 activity in a biological sample comprising one or more peptide substrates disclosed herein. Such a kit may further comprise one or more agents selected from the group consisting of (a) one or more inhibitors of non-MMP activities, (b) one or more inhibitors of MMP activities, (c) one or more inhibitors of non-collagenase 3 MMP activities, (d) one or more activators of MMP activities, (e) one or more further substrates specific for collagenase 3, (f) one or more further substrates specific for a MMP other than collagenase 3, and (g) any one or more of collagenase 3, collagenase 1, gelatinase A, gelatinase B as stromelysin for use as calibration standards. Instructions for using such kits, which contain, for instance, methodology reported herein, may also be included.

For use as inhibitors of non-MMP activities, serine, cysteine and aspartic proteases are well known in the art and may be included in certain embodiments. For instance, SIGMA PROTEASE INHIBITOR COCKTAIL®, catalog No. P8340 may be used. General inhibitors of MMP activities include Chemicon's GM6001 (GALARDIN™), metalloproteinase inhibitor, Ethylene Diamine Tetra Acetic Acid (EDTA), 1,10-O-Phenanthroline, or TAPI™ or TAPI™ derivatives from PEPTIDES INTERNATIONAL, to name a few. Activators of MMP activity include, among others, APMA, proteolytic enzymes of the furin family and membrane bound MMPs (MT-MMPs). Inhibitors of non-collagenase 3 MMP activities include natural substrates for other MMPs, for instance gelatin, type I collagen, type II collagen and fibronectin, among others.

The kits of the invention may be used in methods of measuring MMP enzymes in samples. For instance, the kits may be used to diagnose a disorder or disease or a propensity for disease, comprising testing a biological sample from a patient for aberrant levels of collagenase 3 activity according to instructions provided in said kit. Again, such diseases would include any inflammatory disorder or disease, autoimmune disease, multiple sclerosis, diabetes, cancer, Alzheimer's Disease, stroke, spinal cord injury, central nervous system diseases, rheumatoid arthritis, osteoarthritis, Crohn's disease, glomerular nephritis and restenosis macular degeneration, periodontal disease, chronic obstructive pulmonary disease, asthma, osteoporosis or any disease or disorder of the bones or joints, or any other disease or disorder that might be associated with aberrant levels of MMP enzymes.

The kits described herein could also be used to develop MMP profiles for different disorders, for instance to evaluate the participation or appearance or involvement of certain MMPs in different diseases, or at different times during disease. For instance, such a method might involve (a) testing a biological sample from a patient having said disorder or disease for aberrant levels of MMP activity, including collagenase 3 activity, according to instructions provided in said kit; and (b) comparing the levels of MMP activity including collagenase 3 activity to activities detected in biological samples from one or more other patients in order to develop a MMP profile for said disorder or disease.

In this regard, the substrates reported herein may also be attached to solid supports using any suitable linker, ligand or chemical attachment means, or alternatively may be synthesized directly on a solid support. Also envisioned is a multiwell apparatus or chip containing separate wells or vessels with different MMP substrates, substrate reagents or attached substrates, which may be used for testing a biological fluid or other sample for its MMP profile. "Substrate reagent" means that compounds in addition to the substrate may be included in the "reagent," for instance activators, inhibitors or further substrates as described above. Suitable multiwell plates include 12-, 24-, 96-, 384-well, etc. The size of the chip or multiwell plate or apparatus will depend on how many substrate reagents are to be used to formulate the MMP profile, and what type of reader will be used to interpret the results. For fluorescent substrates for instance, the size of the plate may be dictated by the fluorescent plate reader employed.

Also encompassed are methods of using the kits described herein to monitor progression of a disorder or disease, for instance by (a) testing a biological sample from a patient for aberrant levels of an MMP enzyme such as collagenase 3 according to instructions provided in said kit at the time of diagnosis;

(b) testing a biological sample from said patient for aberrant levels of the enzyme according to instructions provided in said kit at a designated time following diagnosis; and (c) comparing the levels of the MMP detected at the time of diagnosis with the levels of the MMP at the designated time following diagnosis in order to monitor progression of said disease.

Also encompassed is a method of using the kits disclosed herein to monitor progression of a disorder or disease in response to treatment, for instance by (a) testing a biological sample from a patient for aberrant levels of an MMP such as collagenase 3 according to instructions provided in said kit at the time of diagnosis or prior to treatment;

(b) testing a biological sample from said patient for aberrant levels of the MMP according to instructions provided in said kit at a designated time following treatment; and (c) comparing the levels of the MMP detected at the time of diagnosis or prior to treatment with the levels of MMP at the designated time following treatment in order to monitor progression of said disease in response to said treatment.

Also encompassed are isolated nucleic acids encoding the peptide substrates reported herein. Such a nucleic acid may be used to produce the peptide substrate, for instance by expressing the nucleic acid in a host cell. It should be understood that different nucleic acid sequences may encode the same amino acid sequence due to the degeneracy of the triplet code, and that the invention encompasses all possible nucleic acid sequences coding for the peptides described herein.

Using well known cloning techniques, peptide coding sequences may be fused in frame to a signal sequence to allow secretion by the host cell. Alternatively, such peptides may be produced as a fusion to another protein, and thereafter separated and isolated by the use of a site specific protease. Such systems for producing peptides and proteins are commercially available. It will also be feasible to employ such host cells in methods for detecting synthesis of a particular MMP by a test cell or detecting MMP activity in a sample, for instance by mixing a test cell or a sample with a host cell expressing a peptide substrate and detecting cleavage of said peptide substrate, for instance using neo-epitope antibodies specific for cleavage products of said peptide.

Also envisioned are multiple enzyme/multiple substrate embodiments which include methods of determining the concentrations of multiple enzymes in a sample, comprising (a) contacting the sample with multiple substrate reagents; (b) determining the reaction rate for each individual substrate/enzyme interaction; and (c) comparing the determined reaction rates to standard reaction rates based on known quantities of each enzyme to calculate the amount of each enzyme present in said sample. Such methods are applicable to any mixed sample of enzymes, or any non-enzyme system, i.e. catalyzed reactions, for which specific substrates, ligands, etc. are available for measuring the activities of sample components.

More specifically, such multiple enzyme/multiple substrate methods comprise: (a) dividing the sample into a number of portions, the number of portions equaling the number of substrate reagents used;

(b) contacting the sample with multiple substrate reagents, each sample portion contacting one substrate reagent in a separate vessel(well);

(c) determining the reaction rate for each sample portion exposed to its substrate reagent;

(d) contacting known quantities of each enzyme with multiple substrate reagents, each substrate reagent contacting each enzyme in a separate vessel(well);

(e) determining the reaction rate for each enzyme exposed to each individual substrate reagent;

(f) formulating a set of simultaneous equations relating the reaction rates and concentrations of each enzyme to the reaction rate of the sample portion; each equation relating the reaction rates for one of the substrate reagents; and (g) solving the set of simultaneous equations from (f) to calculate the concentration of each tested enzyme present in said sample.

The multiple enzyme/multiple substrate embodiment may be performed with any number of substrate reagents and enzymes. “Substrate reagent” means that compounds in addition to the substrate may be included in the “reagent,” for instance activators, inhibitors or further substrates as described above. Where several substrates and enzymes are used, the calculating step (g) may be performed by a microprocessor, although with lower numbers, such as two enzymes and substrates, calculations may also be performed manually.

One embodiment for the multiple enzyme/multiple substrate comprises a method wherein substrate reagents are selective for different enzymes in said sample. For instance, the method may be used to measure different MMP enzymes, for instance where one enzyme is collagenase 3. Alternatively, the substrate reagents may be more selective for a first enzyme in the mixed sample than a second enzyme, for instance, where such first and second enzymes are MMP enzymes having different levels of specificity for each substrate. For instance, one embodiment illustrated herein uses two peptide substrates that are more selective for collagenase 3 over gelatinase A, however, rates of reaction with the substrates are determined for both enzymes in order to allow the calculation of activities for each enzyme in the mixed sample. Similar assays may be performed with other MMP enzymes, for instance, with gelatinase B, collagenase 1 and stromelysin 1, among others. Such multiple enzyme/multiple substrate assays typically work best when there is an excess of substrate relative to the amount of enzymes to be measured. That way, the contributions of each enzyme are additive, and the enzymes are not competing for the same substrate molecules.

The following is a general guideline for performing the multiple enzyme/multiple substrate methods disclosed herein:

Determination of Enzyme Concentrations in Biological Samples using Multiple Substrates General Approach.

Expose the same biological sample to multiple substrates in separate wells.

Each substrate should have strong specificity for one of the enzymes in the mixture.

For an exact solution, there should be as many substrates as there are enzymes in question. For example, if a sample may have 3 significant enzymes, then 3 substrates/wells will be used. Alternatively, there should be at least as many substrates as there are enzymes being tested.

Record the response (say Fluorescence or Absorbance) as a function of time.

Formulate a set of simultaneous equations relating the response of the sample to the concentration of each enzyme.

Solve the set of equations for the concentration of each enzyme in the sample.

Assumptions

Note that these assumptions are used to simplify the problem. Without these assumptions the problem may still be solvable.

1. At least in the initial stages, response versus time is linear, and proportional to enzyme concentration.
2. Contributions of each enzyme are additive. This should be the case if there is an excess of substrate, so that each enzyme is not competing for the same substrate molecules.
3. Intercept of Response versus time is zero.

Solution

| Let: | |
|---|---|
| Rj | Response of Substrate j |
| Rij | Response of Enzyme i to Substrate j |
| Ci | Concentration of Enzyme i |
| Kij | Proportionality Constant for Response of Enzyme i to Substrate j |
| T | Reaction Time |
| Mj | Response Divided by Time of Substrate j (Symbol used for Convenience) |

Equations:

| | |
|---|---|
| 1. | Rj = Sum(Rij), i = 1 to n |
| 2. | Rij = KijCiT |
| 3. | Rj = Sum(KijCiT), i = 1 to n<br>dividing by T, |
| 4. | Rj/T = Sum(KijCi), i = 1 to n<br>for ease of writing, let Rj/T = Mj, then, |
| 5. | Mj = Sum(KijCi),i = 1 to n<br>or, expanding |
| 6. | Mj = K1jC1 + K2jC2 + K3jC3 + . . . + KnjCn<br>for a simple example, let n = 2, then, |
| 7. | Mj = K1jC1 + K2jC2<br>using two substrates, we let j = 1 to 2 |
| 8. | M1 = K11C1 + K21C2 |
| 9. | M2 = K12C1 + K22C2 |

here, C1 and C2 are unknown concentrations of Enzymes 1 and 2,

K11 . . . K22 are known proportionality Constants, typically determined from the standard curves, M1 . . . M2 are known data points (we know R1 . . . R2 for each time T), thus, we have 2 equations and 2 unknowns, which is solvable. Solving equations 8. and 9. for C1 and C2 we get:

| | |
|---|---|
| 10. | C1 = (M1 − K21C2)/K11 |
| 11. | C2 = (M2K11 − M1K12)/(K22K11 − K12K21) |

A Hypothetical Example.

One example of a Multiple Enzyme Multiple Reagent Assay System would be a 2 Enzyme 2 Substrate System. Let us say we have Enzymes 1 and 2, and Substrates A and B. We react known concentrations of Enzyme 1 with Substrate A and find they produce a Response of 100 counts per hour per unit of Enzyme 1. We react known concentrations of Enzyme 2 with Substrate A and find they produce a Response of 200 counts per hour per unit of Enzyme 2. We react an unknown mixture of Enzyme 1 and Enzyme 2 with Substrate A and find it produces a Response of 400 counts per hour. We do the parallel reactions with Substrate B, and get numbers of 150, 50, and 350 respectively. The Responses are summarized in the Table 1:

TABLE 1

Hypothetical reaction rates of substrates in multiple enzyme/multiple substrate system against individual enzymes and mixed sample

| | Enzyme 1 Response (counts/hr/nM) | Enzyme 2 Response (counts/hr/nM) | Enzyme Mixture Response (counts/hr) |
|---|---|---|---|
| Substrate A | 100 | 200 | 400 |
| Substrate B | 150 | 50 | 350 |

This table can be expressed as a set of 2 equations in 2 unknowns. The unknowns are the concentrations of Enzymes 1 and 2 ($C_1$ and $C_2$ respectively):

$$100C_1+200C_2=400$$

$$150C_1+50C_2=350$$

Solving these equations gives $C_1$=2 nM and $C_2$=1 nM. This approach can be extended to as many Enzymes as desired, but always requires having at least as many Reagents as Enzymes to be measured.

All references and patents cited in this application are incorporated by reference in their entirety. The following examples are merely illustrations of the many embodiments covered by the present invention, and should not be construed as limited the claims in any way. Those of skill in the art upon reading the exemplary embodiments will immediately envision many similar assays and methods which should also be considered as a part of the invention.

EXAMPLES

Example 1

Substrate Specificity Data for Collagenase 3 and the MMPs

Determination of Enzyme Concentration.

In a black coated plate with clear bottom was added the fluorescence substrate, Dabcyl-GPLGMRGC(Fluorescein)-NH2 (SEQ ID NO: 44) or FlSb1 at a concentration of 5-20 μM in the assay buffer that contains: 50 mM Tris, pH 7.5; 200 mM NaCl; 5 mM $CaCl_2$, 10 μM $ZnCl_2$, and 0.01% Brij 35. It was incubated with the appropriate matrix metalloprotease using increasing concentrations of the inhibitor, GM 6001 (GALARDIN™), from Chemicon. The change in fluorescence was monitored with a CYTOFLUOR® fluorimeter from MILLIPORE®. Curves are fitted to the Morrison equation (Morrison, J. F., & Walsh, C. T. (1988) Adv. Enzymol. Relat. Areas Mol. Biol. 61, 202) using the SIGMAPLOT® software, and enzyme concentrations were determined from the fit.

Determination of kcat/Km for Peptide Substrates.

Using Dnp substrate #1, and the enzyme concentrations determined by active site titration with the tight binding inhibitor, GM 6001 (GALARDIN™), from Chemicon, kcat/Km values are calculated for collagenase 3, collagenase 1, gelatinase A and B, and stromelysin 1. Specificity (kcat/Km) can be defined as the fractional turnover of a substrate to a product per unit time per unit of enzyme. The larger a substrate's specificity, the larger its response per unit of enzyme. Large specificities equate to high measurement sensitivity.

The formula used to calculate Substrate Specificity (kcat/Km) was:

ti $kcat/Km=M/(3600*Fe*Ce)$ where

| Symbol | Units | Description |
|---|---|---|
| Kcat/Km | (1/sM) | Specificity Constant |
| M | (counts/hr) | Slope of Net Fluorescence v Time Curve in Early Linear Range (Counts/Hr) |
| Fe | (counts) | Net Increase in Fluorescence Reading at End Point (Maximal Net Fluorescence Counts) |
| Ce | (M) | Concentration of Enzyme in Reaction (Molar) |
| 3600 | (sec/hr) | Conversion Factor (seconds/hour) |

Determination of kcat/Km for Dnp Peptide Substrates.

The Dnp substrates listed in Table 2 are prepared and assayed as described below: Briefly, a dimethylsulfoxide stock of 5 mM peptide was diluted in assay buffer so that the substrate concentration is 25 μM in a 200 μl volume. The assay buffer contained: 50 mM Tris, pH 7.5; 200 mM NaCl; 5 mM $CaCl_2$, 10 μM $ZnCl_2$, and 0.01% Brij 35. After addition of enzyme (0.05 nM, 0.17 nM, 0.17 nM, 10 nM, and 17 nM final concentrations for collagenase 3, gelatinase A, gelatinase B, collagenase 1, and stromelysin 1 respectively) time points were taken at 10 minutes, 30 minutes, 1 hour and 2 hours when a 50 μl aliquot was removed and quenched with 50 μl of 1% HFBA (heptafluorobutyric acid). For collagenase 1 and stromelysin 1, sometimes 100 μl reactions were used and two time points were taken to conserve the amount of enzyme used. Samples were filtered through a MILLIPORE® plate coated with a PVDF membrane, using a vacuum manifold, and then run through a HPLC C-18 column from VYADAC® using a HP1090 HPLC. Turnover of substrates was compared to substrate #1, since the specificity constants against this substrate have already been determined multiple times for collagenase 3, collagenase 1, gelatinase A and B, and stromelysin 1. Using the specificity constant data for substrate #1, the kcat/Km was calculated for the new substrates.

Determination of kcat/Km for Fluorescence Peptide Substrates

Human Collagenase-3 and human Gelatinase-A were thawed from the −80C freezer and diluted with assay buffer (50 mM Tris pH 7.5, 200 mM NaCl, 5 mM $CaCl_2$, 10 uM $ZnSO_4$, 0.01% Brij-35) to achieve the desired concentrations.

Three different fluorescent substrates were used in these experiments, which were labeled as FlSub1, FlSub3, and FlSub4. FlSub1 is Dabcyl-GPLMRGC(Flu)-NH2 (SEQ ID NO: 45). FlSub3 is Dabcyl-GPVNLHGC(Flu)-NH2 (SEQ ID NO: 46). FlSub4 is Dabcyl-GPHPFRGC(Flu)-NH2 (SEQ ID NO: 47). The substrates were thawed from the −80C freezer and diluted with assay buffer (50 mM Tris pH 7.5, 200 mM NaCl, 5 mM $CaCl_2$, 2 uM $ZnSO_4$, 0.02% Brij-35) (200 mM NaCl, 100 mM Tris pH 7.5, 500uM $CaCl_2$, 10 uM $ZnSO_4$, 0.01% Brij-35) to achieve the desired concentrations. Prior to entering the freezer, the substrates were diluted from a dry powder to 5 mM concentration in DMSO. Six substrate mixes were created for each experiment, three with PRIONEX GELATIN®, and three without (de-ionized water added in place of the Gelatin). First, the 5 mM substrates were diluted to 20 uM with assay buffer, and then a 1:250 volume ratio of PRIONEX GELATIN® or deionized $H_2O$ was added.

Reactions were performed in a COSTAR® 96 well plate, black plastic with a transparent flat bottom. All reactions were performed in duplicate. All wells contained 20 ul of the diluted enzyme, and 80 ul of the 20 uM substrate mixture. As a control to determine background fluorescence levels, 2 columns (12 wells total) contained 20 ul of the assay buffer, and 80 ul of the substrate mixture. The enzyme dilutions and assay buffer were added first, and then the substrate mixtures were added using a multipipetter. Immediately after adding the substrates, the plate was inserted into a CYTOFLUOR® fluorescence plate reader. Excitation and emission filters were set to B and B, 485 nm and 530 nm respectively. Sensitivities were set to 1, 2, 3, and 4. Readings were automatically recorded every 10 or 15 minutes for 10 or 15 hours, respectively.

Data from the CytoFluor plate reader was imported directly into a MICROSOFT EXCEL® workbook for analysis. The end result of the analysis is the calculation of the Substrate Specificity (Kcat/Km) and the Substrate Selectivity for each enzyme/substrate pair. To illustrate, let us define Substrate Specificity (Kcat/Km) as: "The Fractional Rate of Conversion of a Substrate to a Product per unit of Enzyme, for a particular Enzyme." The Substrate Specificity has units of (Fractional Turnover)/((Time)*(Enzyme Concentration)), one example being ($M^{-1}s^{-1}$). Let us define Substrate Selectivity as "The Ratio of the Substrate Specificity for Enzyme A to the Substrate Specificity for Enzyme B for a given Substrate." The Substrate Selectivity is unitless.

Any technique used to determine Substrate Specificity requires a few basic pieces of information: the Net Fluorescence at Complete Turnover, the Net Rate of Increase in Fluorescence in the Linear Range, and the Enzyme Concentration in the Reaction Well. The sequence of events in the analysis is: importation of the fluorescence vs time data, combining the duplicated well fluorescence counts into a single averaged value, subtracting the averaged background fluorescence from the averaged total fluorescence in the well to give the net averaged fluorescence, calculation of the slope of the net averaged fluorescence vs time curve, manual determination of the maximum net averaged fluorescence for each enzyme and substrate pair, and finally the calculation of the Substrate Specificity and Selectivity based on the accumulated data. In these experiments, the Selectivities were calculated as the ratio of the Specificity of Collagenase-3 to the Specificity of each of the other Enzymes for a given Substrate.

Specificity and Selectivity Results of Substrates

Dinitrophenyl-labeled (Dnp) and fluorescence substrates were initially selected based on the data provided in Deng et al. (2000) and by BLAST® searches of phage clone sequences. The BLAST searches were performed using the National Center for Biotechnology Information website. The first 12 Dnp and 2 fluorescence substrates were tested to determine their specificity constants for all 5 MMPs, and their and selectivities versus Col-3 were calculated. Based upon this initial data, we designed further substrates to enhance selectivity against the gelatinases. Enzymes were obtained from Dr. Gillian Murphy, University of Angolia, Norwich, UK or purchased from Chemicon and TRIPLE POINT BIOLOGICS. Their concentrations were determined as described in Deng et al., herein incorporated by reference, except that the commercially available tight binding inhibitor, GM 6001, was used to titrate enzyme activity as described above.

Table 2 lists the experimentally determined specificities (kcat/Km) of the substrates for collagenase 3, and the selectivity ratios over gelatinase A and B, collagenase 1, and stromelysin 1. The standard Dnp substrate, Dnp-GPLG-MRG-NH2 (SEQ ID NO: 3), was used as a control to correct for variability in enzyme concentrations from experiment to experiment. Turnover of the Dnp-labeled substrates was followed by high pressure liquid chromatography (HPLC) analysis. For fluorescence substrates, initial velocities were obtained by following the change in fluorescence with time. Fluorescence endpoints were determined by addition of excess collagenase 3 to certain wells, ensuring complete conversion of the substrate. The specificity constants were calculated by dividing the fractional turnover by the enzyme concentration and assay time.

TABLE 2

Specificity and Selectivity Summary
Substrates 1 through 50 versus
Collagenase-3 vs Gelatinase-A, Gelatinase-B, Collagenase-1, Stromelysin-1

| HPLC (Colorimetric) Substrate | Coll-3 Specificity Constant (1/sM) | Gel-A Selectivity v. Coll-3 (unitless) | Gel-B Selectivity v. Coll-3 (unitless) | Coll-1 Selectivity v. Coll-3 (unitless) | Strom-1 Selectivity v. Coll-3 (unitless) |
|---|---|---|---|---|---|
| 1-GPLGMRG* (SEQ ID NO: 3) | 3541390 | 11 | 5 | 347 | 4864 |
| 2-PINLHG* (SEQ ID NO: 48) | 377170 | 9 | 4 | 101 | 824 |
| 3-GPINLHG* (SEQ ID NO: 4) | 699896 | 28 | 15 | 180 | 1114 |
| 4-GPSELKG* (SEQ ID NO: 5) | 862092 | 7 | 4 | 470 | 831 |
| 5-PHPFRG* (SEQ ID NO: 6) | 230151 | 28 | 4 | 2226 | 1046 |
| 6-GPSGIHV* (SEQ ID NO: 8) | 1413523 | 10 | 17 | 1430 | 35695 |
| 7-VTPYNMRG* (SEQ ID NO: 9) | 2690168 | 31 | 4 | 39 | 1004 |
| 8-GPLQFRG* (SEQ ID NO: 10) | 705404 | 32 | 7 | 3685 | 700 |
| 9-GPKGMRG* (SEQ ID NO: 11) | 2324612 | 7 | 3 | 1570 | 13211 |
| 10-GPYGMRA* (SEQ ID NO: 12) | 5658017 | 16 | 6 | 212 | 404 |
| 11-GPKGITS* (SEQ ID NO: 13) | 733630 | 6 | 2 | 548 | 37047 |
| 12-GPRPFRG* (SEQ ID NO: 14) | 633530 | 9 | 4 | 4202 | |
| 1-GPLGMRG | 2175957 | 5 | 2 | 175 | 4254 |
| 13-GPLSISG (SEQ ID NO: 15) | 191351 | 7 | 1 | 11 | |
| 14-GPMSYNG (SEQ ID NO: 16) | 887280 | 5 | 3 | 201 | |
| 15-GPLSFQG (SEQ ID NO: 49) | 453947 | 21 | 5 | 688 | 191 |
| 16-GPLSIQD (SEQ ID NO: 17) | 868299 | 65 | 6 | 45 | 590 |
| 17-GPHPFRG (SEQ ID NO: 7) | 899685 | 17 | 8 | 3346 | 2299 |
| 18-GPSGIHL (SEQ ID NO: 18) | 284040 | 8 | 6 | 3437 | 2045 |
| 19-GPVNLHG (SEQ ID NO: 19) | 1151217 | 25 | 11 | 459 | 1261 |
| 20-PLGMRG (SEQ ID NO: 50) | 979560 | 2 | 1 | 73 | |
| 21-PSGIHL (SEQ ID NO: 51) | 91680 | 2 | 2 | 1323 | |
| 22-GPLGMRG (SEQ ID NO: 3) + H2O | 3161595 | 6 | 2 | 245 | |
| 23-GPLGMRG (SEQ ID NO: 3) + 1:1 Gelatin | 340286 | 41 | 5 | 91 | |
| 24-GPLGMRG (SEQ ID NO: 3) + 1:4 Gelatin | 562409 | 46 | 5 | 96 | |
| 25-GPLGMRG (SEQ ID NO: 3) + 1:16 Gelatin | 1925546 | 84 | 13 | 215 | |
| 26-GPLGMRG (SEQ ID NO: 3) + 1:64 Gelatin | 2669718 | 69 | 13 | 236 | |
| 27-GPLGMRG (SEQ ID NO: 3) + 1:256 Gelatin | 4651781 | 73 | 18 | 378 | |
| 1-GPLGMRG (SEQ ID NO: 3) | 2353285 | 7 | 2 | 591 | 2006 |
| 28-GPFGLKG (SEQ ID NO: 21) | 1275616 | 26 | 3 | 408 | 1377 |
| 29-GPHPMRG (SEQ ID NO: 22) | 2332400 | 12 | 4 | 526 | 287 |
| 30-GPLQMRG (SEQ ID NO: 23) | 885287 | 15 | 1 | 290 | 311 |
| 31-DEGPMGLKC(Me)YLG (SEQ ID NO: 24) | 528040 | 9 | 4 | 452 | 468 |
| 32-GPVNLHGRC(Me) (SEQ ID NO: 52) | 1035753 | 9 | 2 | 2119 | 510 |
| 33-GPVNLHGC(Me) (SEQ ID NO: 53) | 813197 | 15 | 3 | 1391 | 770 |
| 34-VC(Me)PKGITSC(Me)VFR (SEQ ID NO: 26) | 1540003 | 7 | 1 | 215 | 835 |
| 1-GPLGMRG (SEQ ID NO: 3) | 4152637 | 9 | 8 | 757 | 3367 |
| 1-GPLGMRG (SEQ ID NO: 3) | 4138106 | 12 | 16 | 155 | 6248 |
| 1-GPLGMRG (SEQ ID NO: 3) | 4543053 | 25 | 4 | 184 | 7749 |
| 35-GPLGLHGC(Me)* (SEQ ID NO: 54) | 3731241 | 16 | 5 | 660 | 10434 |
| 36-GPLGFRGC(Me)* (SEQ ID NO: 55) | 2398990 | 10 | 7 | 10561 | 7288 |
| 37-GPLGFRVC(Me)* (SEQ ID NO: 56) | 3915950 | 15 | 20 | 17330 | 3968 |
| 38-GPLPFHVC(Me)* (SEQ ID NO: 57) | 597697 | 20 | 18 | 2949 | 619 |
| 39-GPSPFHVC(Me)* (SEQ ID NO: 58) | 337770 | 18 | 54 | 1567 | 2098 |
| 40-GPSPLHGC(Me)* (SEQ ID NO: 59) | 1761804 | 8 | 7 | 274 | 2990 |

TABLE 2-continued

Specificity and Selectivity Summary
Substrates 1 through 50 versus
Collagenase-3 vs Gelatinase-A, Gelatinase-B, Collagenase-1, Stromelysin-1

| HPLC (Colorimetric) Substrate | Coll-3 Specificity Constant (1/sM) | Gel-A Selectivity v. Coll-3 (unitless) | Gel-B Selectivity v. Coll-3 (unitless) | Coll-1 Selectivity v. Coll-3 (unitless) | Strom-1 Selectivity v. Coll-3 (unitless) |
|---|---|---|---|---|---|
| 41-GPVNFRVC(Me) 5 uM (SEQ ID NO: 60) | 2568454 | 88 | 217 | | 400 |
| 42-GPAPFRGC(Me)* (SEQ ID NO: 61) | 1142237 | 9 | 14 | 4415 | 488 |
| 43-GPAPFRVC(Me)* (SEQ ID NO: 62) | 1762709 | 37 | 82 | 5788 | 448 |
| 44-GPAPLHGC(Me)* (SEQ ID NO: 63) | 1686089 | 12 | 10 | 473 | 620 |
| 45-GPLPFRGC(Me)* (SEQ ID NO: 64) | 972806 | 16 | 8 | 429 | 814 |
| 46-GPLPFRVC(Me)* (SEQ ID NO: 65) | 1291061 | 36 | 21 | 550 | 332 |
| 47-GPSPFRGC(Me)* (SEQ ID NO: 66) | 1303116 | 10 | 13 | 2426 | 1394 |
| 48-GPAPLHVC(Me)* (SEQ ID NO: 67) | 676623 | 12 | 11 | 126 | 264 |
| 49-GPLGLHVC(Me)* (SEQ ID NO: 68) | 4460584 | 32 | 26 | 182 | 12711 |
| 50-GPLPLHGC(Me)* (SEQ ID NO: 69) | 1103710 | 20 | 10 | 36 | 986 |

Note:
Every substrate has a Dnp (Dinitrophenyl) at the N-terminus, and ends with an amide at the C-terminus.
*Items ending with an asterisk represent average values Our original hypothesis proposed that extending the amino acid sequence to a 12 mer using the data obtained from BLAST® searches of the phage clone sequences might provide for more selective substrates of collagenase 3. A fluorescence substrate based on the sulfate transporter was prepared and the kcat/Km against the five MMPs was determined. Surprisingly, the substrate Dab-SYPSGIHLC(Flu)LQR-$NH_2$(FlSb2) (SEQ ID NO: 27), was less selective than the substrate based on the consensus sequence from the phage display data, Dab-GPLGMRGC(Flu)-$NH_2$ (FlSb1) (SEQ ID NO: 44). In addition the sulfate transporter-based substrate was 100-fold less sensitive for collagenase 3 compared to the consensus substrate (#1 above).

We further confirmed that longer substrates did not confer better selectivity by measuring the specificity constants of two Dnp-labeled substrates, #31 and #34. The 7 mer substrate, Dnp-GPKGITS-$NH_2$ (#11) (SEQ ID NO: 13), had the same selectivity profile compared to the 12 mer substrate, Dnp-VC(Me)PKGITSC(Me)VFR-NH2 (#34) (SEQ ID NO: 26). Furthermore, in the case of the sulfate transporter substrate, elongation, and modification of the sequence proved to be detrimental to the goal of enhancing specificity (e.g., compare substrate #18, Dnp-GPSGIHL-$NH_2$, with fluorescence substrate Dab-SYPSGIHLC(Flu)LQR-$NH_2$ (SEQ ID NO: 27)).

Even though the longer substrates were not necessarily better, the BLAST searches provided an opportunity to prepare substrates with unique sequences that sometimes did prove to be very selective. For instance, substrate #19 Dnp-GPVNLHG-$NH_2$ (SEQ ID NO: 19) came from a BLAST search and is one of the most selective substrates identified (see Table 2).

Two structure activity relationships (SAR) came out of this data. The first is that glycine at position P4 to the substrate cleavage sequence increases the reactivity towards collagenase 3 and sometimes leads to better specificity over the other MMPs (see substrate #20 versus substrate #1 and substrate #2 versus substrate #3). Second, valine at P3' in some substrates increases the selectivity of the substrate over stromelysin and the gelatinases and further improves activity against collagenase 3 (e.g., compare substrate #6 over substrate #18).

Example 2

Inhibition of Gelatinases with Gelatin and Type II Collagen

Initial experiments with fluorescence substrate 1 and synovial fluids indicated that there was very little fluorescence change, even with a 1:1 ratio of fluid to substrate. More importantly, of the fluorescence change observed, only a small portion was MMPI inhibitable. Therefore, we performed experiments to see if we could increase MMP activity using APMA pre-incubation. Two hour room temperature activation proved optimal. At this point, while MMP activity was increased, a substantial contribution appeared to be coming from the gelatinases. Since we were trying to measure collagenase 3 levels, we needed a technique to reduce the gelatinase activity.

Inhibition with Gelatin

We found that adding about a 1:300 ratio of PRIONEX GELATIN® gelatin to the substrate mixture selectively inhibited the gelatinases over collagenase 3 in the fluorescence experiments (Table 3). For instance, based on the substrate results in Table 2, two fluorescence substrates that were based on substrates #17 and #19, fluorescence substrate Dab-GPVNLHGC(Flu)-NH2(FlSb3) (SEQ ID NO: 46) and fluorescence substrate Dab-GPHPFRGC(Flu)-NH2(FlSb4) (SEQ ID NO: 47) were prepared. Below in Table 3 are the specificity constants for fluorescence substrates 1, 3 and 4 in the presence and absence of PRIONEX GELATIN®.

TABLE 3

| Experimental Results | | | | | |
|---|---|---|---|---|---|
| Substrate (name) | Col-3 Specificity Constant (1/sM) | Gel-A Selectivity v Col-3 (unitless) | Gel-B Selectivity v Col-3 (unitless) | Col-1 Selectivity v Col-3 (unitless) | Strom1 Selectivity v Col-3 (unitless) |
| FISb1 | 4.40E+06 | 19 | 6.5 | 710 | 3665 |
| FISb1 | 1.62E+06 | 3.9 | 1.2 | 72.6 | 707.5 |
| FISb1 + Gel | 1.74E+06 | 25.8 | 6.3 | 78.4 | 769.1 |
| FISb3 | 4.21E+05 | 2.3 | 0.7 | 128.5 | 71.3 |
| FISb3 + Gel | 4.71E+05 | 26.5 | 6.0 | 92.3 | 72.5 |
| FISb4 | 3.27E+04 | 14.8 | 2.6 | 87.8 | 43.9 |
| FISb4 + Gel | 2.69E+04 | −121.2 | 11.6 | 168.5 | 53.8 |

FlSb4 has improved selectivity over the gelatinases relative to FlSb1, and gelatin addition enhances this effect. The substrate selectivities for stromelysin 1 using FlSb 3 and 4 relative to FlSb1, however, is reduced approximately 10 fold. These substrates may be useful for directly measuring collagenase 3 activity, or can be used in combination as discussed for multiple substrates with multiple unknowns (see below).

Experiments with HPLC/Dnp/Colorimetric substrates were also performed (See Table 2). In these experiments, the reactions contained 20 ul enzyme reagent, 90 ul substrate, and 40 ul of serially diluted PRIONEX GELATIN®. Thus, the ratio of total substrate mixture volume to diluted PRIONEX GELATIN® volume was 130 ul:40 ul=3.25. Multiplying the stated ratios in Table 2 by 3.25 gives: 1:1 becomes 1:3.25, 1:4 becomes 1:13, 1:16 becomes 1:52, 1:64 becomes 1:208, and 1:256 becomes 1:832. These were the volumetric ratios of PRIONEX GELATIN® volume to Substrate Mixture volume. Looking at the total reaction volume (versus substrate mixture volume), we get 150 ul:40 ul=3.75. Multiplying the stated ratios in Table 2 by 3.75 gives: 1:1 becomes 1:3.75, 1:4 becomes 1:15, 1:16 becomes 1:60, 1:64 becomes 1:240, and 1:256 becomes 1:960, which were the actual volumetric ratios of PRIONEX GELATIN® volume to total reaction volume used in these experiments.

Inhibition with Type II Collagen.

In a 96 well plate, collagenase 3 (0.013 nM), collagenase 1 (1.25 nM), stromelysin 1 (0.8 nM), gelatinase A (0.025 nM), or gelatinase B (0.008 nM) were reacted with 20 uM FlSub3 in standard assay buffer in the presence of varying concentrations of bovine type II collagen (0.18-44 ug/ml). The type II collagen, a 1 mg/ml stock in 0.5M acetic acid, was transferred into assay buffer by passing the material through a biospin P6 column from Amersham. The reaction was initiated by addition of substrate to enzyme containing either buffer or an appropriate amount of type II collagen. Data points were taken every 15 min over a period of 15 hours using an excitation and emission wavelength of 350 and 485 nm respectively. The usable data (1-6 hours), was taken and the percent inhibition by type II collagen was calculated for each enzyme and plotted as a function of inhibitor concentration and time in the assay. It should be noted that the percent inhibition varies with time as the bovine substrate is consumed during the reaction course.

Type II collagen is a substrate for collagenase 1 and 3 in its triple helical form. However, in an unexpected result, inhibition by type II collagen of collagenase 3 was not observed (see Table 4 below). For example, activation, rather than inhibition, of collagenase 3 resulted at the highest concentrations of type II collagen. A small but significant inhibition by type II collagen was noted for collagenase 1 at early timepoints. An exciting but unexpected result came in the reactions with the gelatinases. Almost complete inhibition of gelatinase A and B was observed at the highest concentration of type II collagen (0.44 ug/ml) throughout the six hour time course (see Tables 5 and 6).

The impressive inhibition of the gelatinases could be due to the fact that the collagen, in its triple helical structure is able to bind the gelatinases, but the gelatinases are unable to use it as a substrate, unless it is unwound. At the highest concentration of collagen, the selectivity vs the gelatinases improved approximately 80 fold. A modest four fold increase in selectivity was observed for collagenase 1 and stromelysin 1. Note that the increase in selectivity of collagenase 1 and stromelysin 1 is due to the increase in specificity of collagenase 3, by a factor of 2.5, rather than their inhibition. These results along with the results from the PRIONEX GELATIN® experiments, confirm that full length substrates for the MMPs can be used as inhibitors to improve the selectivities of the substrates against a particular enzyme.

TABLE 4

| For Time Period 0.85 to 2.10 Hours Substrate + Inhibitor Concentration | Col-3 Specificity Constant (1/sM) | Gel-A Selectivity v Col-3 (unitless) | Gel-B Selectivity v Col-3 (unitless) | Col-1 Selectivity v Col-3 (unitless) | Strom1 Selectivity v Col-3 (unitless) |
|---|---|---|---|---|---|
| FISb8 (FISb3 + 44 ug/ml TIICol) | 2.55E+06 | 464.6 | 58.8 | 424 | 476 |
| FISb9 (FISb3 + 15 ug/ml TIICol) | 2.25E+06 | 75.9 | 15.2 | 355 | 447 |
| FISb10 (FISb3 + 4.9 ug/ml TIICol) | 1.88E+06 | 26.3 | 5.7 | 265 | 335 |
| F1Sb11 (FISb3 + 1.6 ug/ml TIICol) | 1.54E+06 | 9.3 | 3.0 | 227 | 389 |
| FISb12 (FISb3 + .55 ug/ml TIICol) | 1.47E+06 | 9.9 | 2.2 | 221 | 281 |
| FISb13 (FISb3 + .18 ug/ml TIICol) | 1.33E+06 | 7.7 | 1.8 | 190 | 263 |
| FISb3 | 1.11E+06 | 5.8 | 1.3 | 166 | 192 |
| Improvement In Selectivity for 44 ug/ml Type II Collagen vs no Type II Collagen | | 80 fold | 46 fold | 2.5 fold | 2.5 fold |

TABLE 5

| Percent Inhibition by Type II Collagen. | | | | | | |
|---|---|---|---|---|---|---|
| Type II Collagen Concentration (ug/ml) → | 44.00 | 14.67 | 4.89 | 1.63 | 0.54 | 0.18 |
| | Average Percent Inhibition from 1.1 to 6.6 Hours | | | | | |
| COL3(.013 nM) | −53 | −44 | −28 | −11 | −11 | −8 |
| COL1(1.25 nM) | 15 | 10 | 2 | 0 | 3 | 0 |
| GELA(.025 nM) | 83 | 56 | 32 | −52 | 6 | 2 |

TABLE 5-continued

| Percent Inhibition by Type II Collagen. | | | | | | |
|---|---|---|---|---|---|---|
| Type II Collagen Concentration (ug/ml) → | 44.00 | 14.67 | 4.89 | 1.63 | 0.54 | 0.18 |
| GELB(.008 nM) | 84 | 65 | 38 | 12 | 9 | 9 |
| STR1(.80 nM) | 19 | 18 | 12 | 19 | 13 | 15 |

TABLE 6

| | Average Percent Inhibition for Stated Hours | | | | | | |
|---|---|---|---|---|---|---|---|
| From Hour → | 0.10 | 1.10 | 2.10 | 3.10 | 4.10 | 5.10 | 1.10 |
| To Hour → | 1.10 | 2.10 | 3.10 | 4.10 | 5.10 | 6.10 | 6.60 |
| COL3(.013 nM)-TypeIICOL(44 ug/ul)-FISb3 | 2 | −55 | −71 | −60 | −49 | −41 | −53 |
| COL1(1.25 nM)-TypeIICOL(44 ug/ul)-FISb3 | 50 | 29 | 18 | 12 | 9 | 7 | 15 |
| GELA(.025 nM)-TypeIICOL(44 ug/ul)-FISb3 | 58 | 78 | 86 | 87 | 85 | 82 | 83 |
| GELB(.008 nM)-TypeIICOL(44 ug/ul)-FISb3 | 41 | 82 | 87 | 87 | 85 | 83 | 84 |
| STR1(.80 nM)-TypeIICOL(44 ug/ul)-FISb3 | 62 | 32 | 18 | 14 | 14 | 14 | 19 |
| COL3(.013 nM)-TypeIICOL(15 ug/ul)-FISb3 | 6 | −48 | −59 | −50 | −41 | −34 | −44 |
| COL1(1.25 nM)-TypeIICOL(15 ug/ul)-FISb3 | 44 | 21 | 12 | 8 | 6 | 4 | 10 |
| GELA(.025 nM)-TypeIICOL(15 ug/ul)-FISb3 | 56 | 64 | 70 | 64 | 53 | 41 | 56 |
| GELB(.008 nM)-TypeIICOL(15 ug/ul)-FISb3 | 57 | 67 | 72 | 69 | 64 | 59 | 65 |
| STR1(.80 nM)-TypeIICOL(15 ug/ul)-FISb3 | 57 | 28 | 18 | 14 | 13 | 14 | 18 |
| COL3(.013 nM)-TypeIICOL(4.9 ug/ul)-FISb3 | 8 | −31 | −38 | −31 | −25 | −21 | −28 |
| COL1(1.25 nM)-TypeIICOL(4.9 ug/ul)-FISb3 | 37 | 13 | 3 | 0 | −2 | −4 | 2 |
| GELA(.025 nM)-TypeIICOL(4.9 ug/ul)-FISb3 | 37 | 43 | 46 | 37 | 27 | 19 | 32 |
| GELB(.008 nM)-TypeIICOL(4.9 ug/ul)-FISb3 | 35 | 43 | 47 | 41 | 35 | 30 | 38 |
| STR1(.80 nM)-TypeIICOL(4.9 ug/ul)-FISb3 | 50 | 23 | 11 | 8 | 8 | 8 | 12 |
| COL3(.013 nM)-TypeIICOL(1.6 ug/ul)-FISb3 | 16 | −4 | −15 | −13 | −12 | −11 | −11 |
| COL1(1.25 nM)-TypeIICOL(1.6 ug/ul)-FISb3 | 19 | 6 | 0 | −2 | −3 | −4 | 0 |
| GELA(.025 nM)-TypeIICOL(1.6 ug/ul)-FISb3 | −27 | 4 | −11 | −37 | −68 | −104 | −52 |
| GELB(.008 nM)-TypeIICOL(1.6 ug/ul)-FISb3 | −28 | 14 | 19 | 15 | 11 | 7 | 12 |
| STR1(.80 nM)-TypeIICOL(1.6 ug/ul)-FISb3 | −10 | 24 | 22 | 18 | 17 | 16 | 19 |
| COL3(.013 nM)-TypeIICOL(.55 ug/ul)-FISb3 | 14 | −11 | −15 | −12 | −10 | −10 | −11 |
| COL1(1.25 nM)-TypeIICOL(.55 ug/ul)-FISb3 | 15 | 6 | 3 | 2 | 1 | 1 | 3 |
| GELA(.025 nM)-TypeIICOL(.55 ug/ul)-FISb3 | 2 | 11 | 12 | 8 | 4 | −1 | 6 |
| GELB(.008 nM)-TypeIICOL(.55 ug/ul)-FISb3 | 3 | 10 | 12 | 10 | 8 | 6 | 9 |
| STR1(.80 nM)-TypeIICOL(.55 ug/ul)-FLSb3 | 43 | 26 | 14 | 10 | 8 | 8 | 13 |
| COL3(.013 nM)-TypeIICOL(.18 ug/ul)-FISb3 | 6 | −9 | −10 | −8 | −7 | −6 | −8 |
| COL1(1.25 nM)-TypeIICOL(.18 ug/ul)-FISb3 | 17 | 3 | 0 | −1 | −1 | −1 | 0 |
| GELA(.025 nM)-TypeIICOL(.18 ug/ul)-FISb3 | 3 | 9 | 7 | 3 | 0 | −3 | 2 |
| GELB(.008 nM)-TypeIICOL(.18 ug/ul)-FISb3 | 3 | 12 | 11 | 9 | 7 | 5 | 9 |
| STR1(.80 nM)-TypeIICOL(.18 ug/ul)-FISb3 | 22 | 22 | 15 | 12 | 12 | 12 | 15 |

Example 3

Assay of Biological Fluids Using Fluorescence Substrate 1

To test human sera, serum samples were obtained from OA (osteoarthritis), RA (rheumatoid arthritis), and RP (Relapsing Polychondritis) patients. RP (Relapsing Polychondritis) is an autoimmune disease characterized by breakdown of Type II collagen. Patients with this condition have tested positive for collagenolytic activity using the u-TIINE assay with urine, and by detection of Type II collagen antibodies in serum. Westerns of the RP samples may also be performed to determine if col-3 is present, and if so, discover how much is in the active versus inactive (pro) form. It should be noted that the u-TIINE assay is a composite measure of all the collagenolytic activity in a urine sample.

Methods

Prior to the fluorescence reaction, the biological fluids were incubated with APMA to activate the MMPs (1.5 ul of APMA (Amino Phenyl Mercuric Acid, 100 mM in DMSO) was added to 100 ul of each of the biological fluids for about 2 hours at room temperature). Then the biological fluid and Fluorescent Substrate were combined in a reaction well and the Fluorescence Counts versus Time were recorded. Other wells contained varied known concentrations of MMP Enzymes with the Substrate. Wells with just assay buffer and Substrate were included to provide a background fluorescence level. All fluids were run with and without an MMP inhibitor to determine the amount of the Net Fluorescence due to MMP activity. Calculation of MMP concentrations was based on a comparison of the slope of the Net MMP Inhibitable Fluorescence versus Time curve of the Biological Fluid with that of the known MMP Enzyme concentrations.

Two different fluorescent substrates were used in these experiments, which were labeled as FlSub1 and FlSub3. FlSub1 is Dabcyl-GPLMRGC(Flu)-NH2 (SEQ ID NO: 45). FlSub3 is Dabcyl-GPVNLHGC(Flu)-NH2 (SEQ ID NO: 46). The substrates were thawed from the −80C freezer and diluted with assay buffer (50 mM Tris pH 7.5, 200 mM NaCl, 5 mM $CaCl_2$, 10 uM $ZnSO_4$, 0.01% Brij-35) to achieve the desired concentrations. Prior to entering the freezer, the substrates were diluted from a dry powder to 5 mM concentration in DMSO. Four substrate mixes were created for each experiment, two with MMPI (Matrix MetalloProtease Inhibitor, GM6001), and two without (DMSO used in place of MMPI). All substrate mixes contain Protease Inhibitor Cocktail and PRIONEX GELATIN®. Approximate volume ratios of each of the principal additives in the substrate mix are: MMPI (1:200), Protease Inhibitor Cocktail (1:125), PRIONEX GELATIN® (1:250). Approximate volume ratios of each of the principal additives in the reaction well are: MMPI (1:160), Protease Inhibitor Cocktail (1:100), Prionex Gelatin® (1:200). The substrate mixtures were:

Substrate Mixture A: Fluor Sub1 [Plain+Gelatin] 3200 ul Substrate 20 uM (3187 ul Buffer+12.8 ul 5000 uM Substrate), 25.6 ul Protease Inhibitor Cocktail (1:1), 16 ul DMSO, 12.8 ul PRIONEX GELATIN® (1:1).

Substrate Mixture B: Fluor Sub1 [MMPI+Gelatin] 3200 ul Substrate 20 uM (3187 ul Buffer+12.8 ul 5000 uM Substrate), 25.6 ul Protease Inhibitor Cocktail (1:1), 16 ul MMPI, 12.8 ul PRIONEX GELATIN® (1:1).

Substrate Mixture C: Fluor Sub3 [Plain+Gelatin] 3200 ul Substrate 20 uM (3187 ul Buffer+12.8 ul 5000 uM Substrate), 25.6 ul Protease Inhibitor Cocktail (1:1), 16 ul DMSO, 12.8 ul PRIONEX GELATIN® (1:1).

Substrate Mixture D: Fluor Sub3 [MMPI+Gelatin] 3200 ul Substrate 20 uM (3187 ul Buffer+12.8 ul 5000 uM Substrate), 25.6 ul Protease Inhibitor Cocktail (1:1), 16 ul MMPI, 12.8 ul PRIONEX GELATIN® (1:1).

The reaction was performed in a CoStar 96 well plate, black plastic with a transparent flat bottom. All wells contained 20 ul of a biological fluid (or Collagenase-3 enzyme standard dilutions or Assay Buffer), and 80 ul of one the 20 uM substrate mixtures. As a control to determine background fluorescence levels, 2 columns (8 wells total) contained 20 ul of the assay buffer, and 80 ul of the substrate mixture. The biological fluid, Collagenase-3 standard dilutions, and assay buffer were added first, and then the substrate mixtures were added using a multipipetter. Immediately after adding the substrates, the plate was inserted into a CYTOFLUOR® fluorescence plate reader. Excitation and emission filters were set to B and B, 485 nm and 530 nm respectively. Sensitivities were set to 1, 2, 3, and 4, and a reading was automatically recorded every 10 minutes.

Figure 2:
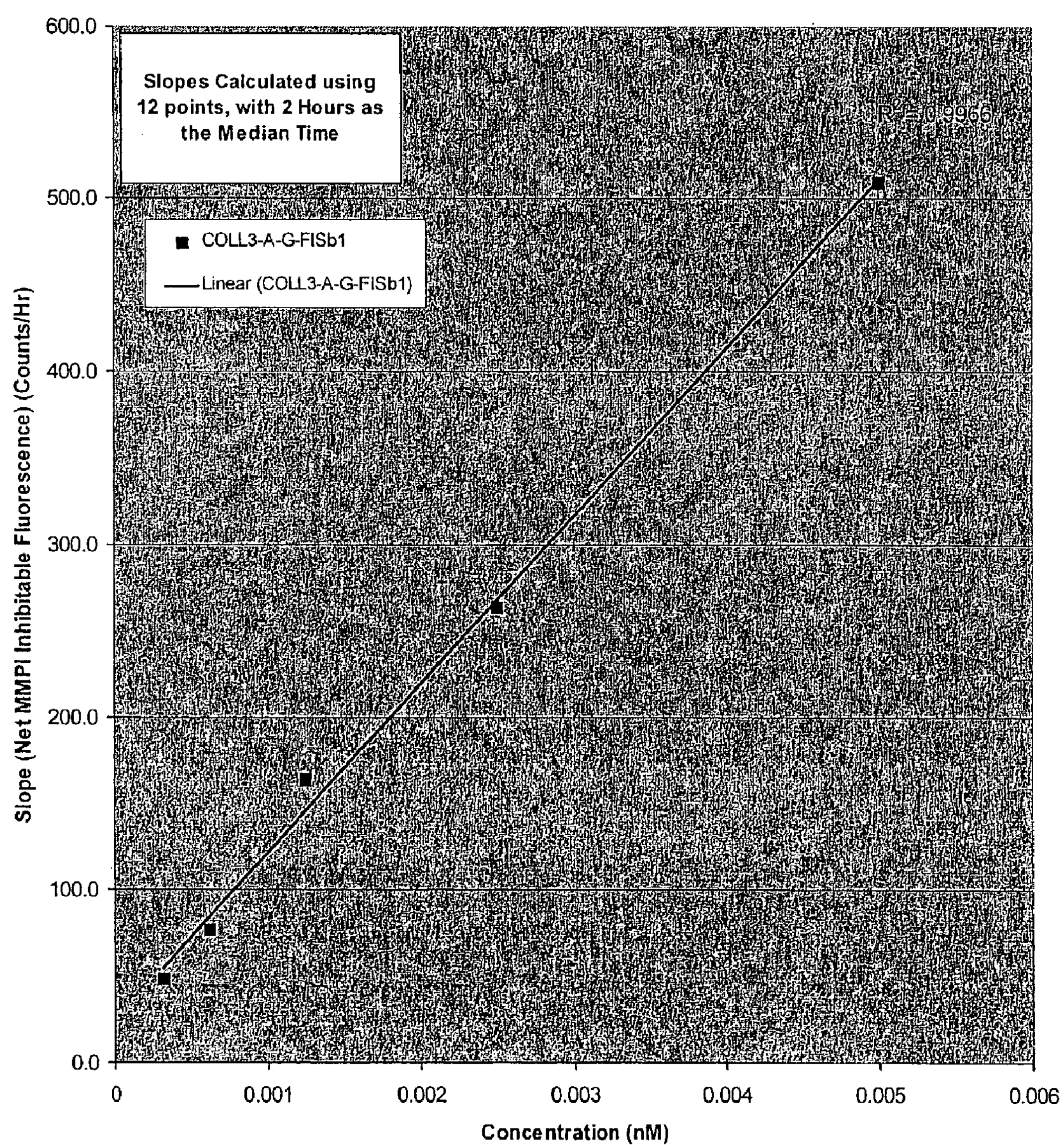
FIG. 2. Standard curve based on the net MMPI inhibitable fluorescence versus concentration of collagenase 3 as measured with fluorescence substrate 1 in the presence of 1:250 gelatin.

Data from the CYTOFLUOR® plate reader was imported directly into a MICROSOFT EXCEL® workbook for analysis. The end result of the analysis is the calculation of the Collagenase-3 concentration, assuming that all MMPI inhibitable activity is due to Collagenase-3. The sequence of events in the analysis is: importation of the fluorescence vs time data, subtracting the background fluorescence from the total fluorescence in the well to give the net fluorescence, subtraction of the net fluorescence of the MMPI inhibited well from the corresponding uninhibited well giving the net MMPI inhibitable fluorescence, calculation of the slope of the net MMPI inhibitable fluorescence vs time curve, and finally comparison of the slope of the net MMPI inhibitable fluorescence vs time curve for the biological fluids with that of the Collagenase-3 standards In short, we found collagenolytic activity in RP serum samples (FIG. 1). Collagenase 3 concentrations were calculated based upon a standard curve generated in this experiment where it was assumed that the MMPI inhibitable fluorescence is due primarily to Col-3. This assumption is made more valid by the inhibition of the Gelatinases by addition of Gelatin. Collagenase 3 concentrations in our biological samples are shown in Table 7. The standard curve is shown in FIG. 2.

TABLE 7

Concentrations of Collagenase 3 in Biological Fluids

| Biological Fluid | 2 Hour Calculated Collagenase-3 Concentration in Biological Fluid (pg/ml) |
|---|---|
| Serum-OA2 | 13 |
| Serum-RA1 | 42 |
| Serum-RP3 | 153 |
| Serum-RP4 | 137 |
| Serum-RP5 | 194 |
| Serum-NO1 | 16 |
| Serum-NO2 | 31 |
| Serum-NO3 | 52 |
| Synovial Fluid-OA1 | 472 |
| Synovial Fluid-OA3 | 238 |
| Synovial Fluid-RA1 | 380 |
| Synovial Fluid-RA2 | 442 |

This experiment provided encouraging results. If all the activity in the synovial fluid samples was due to collagenase 3, there was a substantial amount of activity, roughly equivalent to 0.005 nM enzyme. However, of this activity, approximately 50% was due to MMPs. HPLC experiments show that the non-MMP activity cleaves the substrate at a different location than the MMP activity (as evidenced by separate HPLC peaks). In the fluorescence experiments, we use the presence or absence of MMPI Inhibitor to distinguish between the activities. MMP activity is quantified as Collagenase 3 concentrations in Table 7. Based on this data, it is a reasonable assumption to attribute the MMP activity to Collagenase 3 for several reasons:

Fluorescence Substrate 1 is 215 and 3665 more selective towards Col-3 than Col-1 and Strom-1. This greatly reduces any fluorescence due to those 2 MMPs.

Addition of Prionex Gelatin to the substrate mix reduces MMP activity due to Gelatinases A and B.

Since the Gelatinases take longer to activate with APMA, say 6 hours versus 1 to 2 hours for Col-3, MMP activity early in the reaction is more likely due to Col-3 than to the Gelatinases.

Interesting results were also obtained from the serum samples. At the 2 hour time point, the serum samples had about ⅓ of the total activity and MMPI-inhibitable activity when compared with the synovial fluids. The RP samples have the highest MMP activities. One particular OA sample (OA2), showed MMP levels equal to or lower than Normal serum. A previous OA sample that is in short supply showed higher MMP activity. In fact, OA1 was the only serum that showed MMP activity (~35% inhibitable) prior to APMA activation. This sample had high COMP levels, a marker indicating active disease.

A very significant finding of the fluorescence experiments was the extent of sensitivity observed. We included Col-3 at 0.31 pM (pico Molar) (17 pg/ml) as our lowest standard. When run at a sensitivity of 3, the Net MMP Fluorescence versus Time curve is very linear with a curve fit $R^2$ value of 0.995 for the entire curve, and 0.999 for the final 14 hours (the initial response of all of samples has a slight curvature). Since our plate reader has sensitivities (gains) up to 10, we should be able to detect concentrations well below the fractional pico Molar values that have been demonstrated.

Comparative Example 4

Assays of Biological Fluids Using the Amersham Col-3 Kit

As a comparison for determining Collagenase 3 levels, we tested our biological fluids with an Amersham COL-3KIT®. This kit uses an antibody specific to Col-3 to pull the MMP away from contaminating activities in the fluid. In the first step of the assay, antibody is added and preincubated, causing it to bind to the plate. Then, samples containing Collagenase 3 are added. After incubation periods of up to 12 hr, the fluids are removed, the wells are washed, and a proprietary substrate is added. The Col-3 bound to the plate processes the substrate, resulting in color development. At that point, the absorbance is measured with a plate reader. Before addition of substrate, the Collagenase 3 attached to the plate can be activated to the mature form by addition of APMA. This allows discrimination of the active versus inactive enzyme in the sample. The spec sheet for this product advertises a sensitivity ranging from 0.7-24 ng/ml for this kit, which might be extrapolated via the standard curve to a lower limit of 0.6 ng/ml, although such extrapolation would jeopardize accuracy. It is noteworthy that the kit does cross-react 10% with collagenase 1 and the gelatinases according to the spec sheet. Presumably, the antibody or substrate is not totally specific for collagenase 3.

Figure 3A:
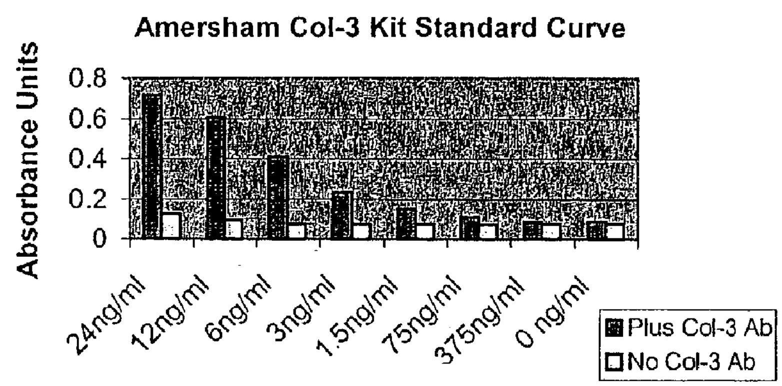
FIG. 3. Graph showing results achieved with Amersham Col-3 kit with and without the supplied Col-3 antibody. (A) Standard curve generated with concentrations of collagenase 3 ranging from 0 to 24 ng/ml; (B) Absorbances detected with Amersham kit for serum and synovial fluid from OA, RA and RP patients.
Figure 3B:
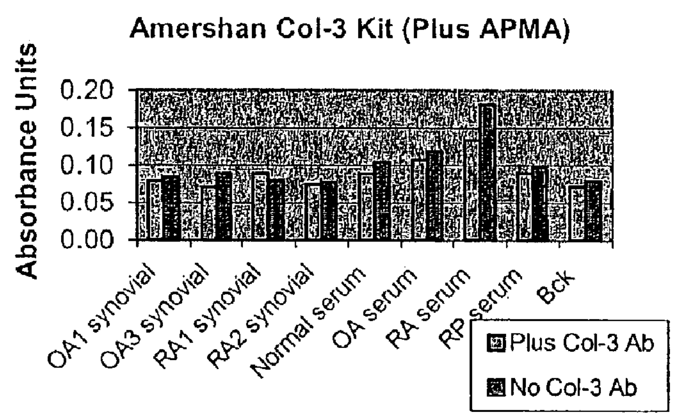

We followed the kit directions but as a control, the antibody was left out of the one half of the wells and antibody assay buffer was put in its place. Each well contained 20 μl of biological fluid, and 80 μl of assay buffer. The buffer contains 50 mM Tris, pH 7.5, 200 mM NaCl, 5 mM $CaCl_2$, 10 μM $ZnCl_2$, and 0.01% brij-35. In the presence of antibody, the standard curve appeared to work well. However, in the absence of antibody, the absorbance readings were higher than background levels in the 24 and 12 ng/ml wells. The biological fluid samples also had absorbance readings above background. However, they showed no difference whether they were incubated with or without the Col-3 antibody. This was true for samples APMA activated (as seen in FIG. 3) or non-activated (data not shown).

Example 5

Figure 4:
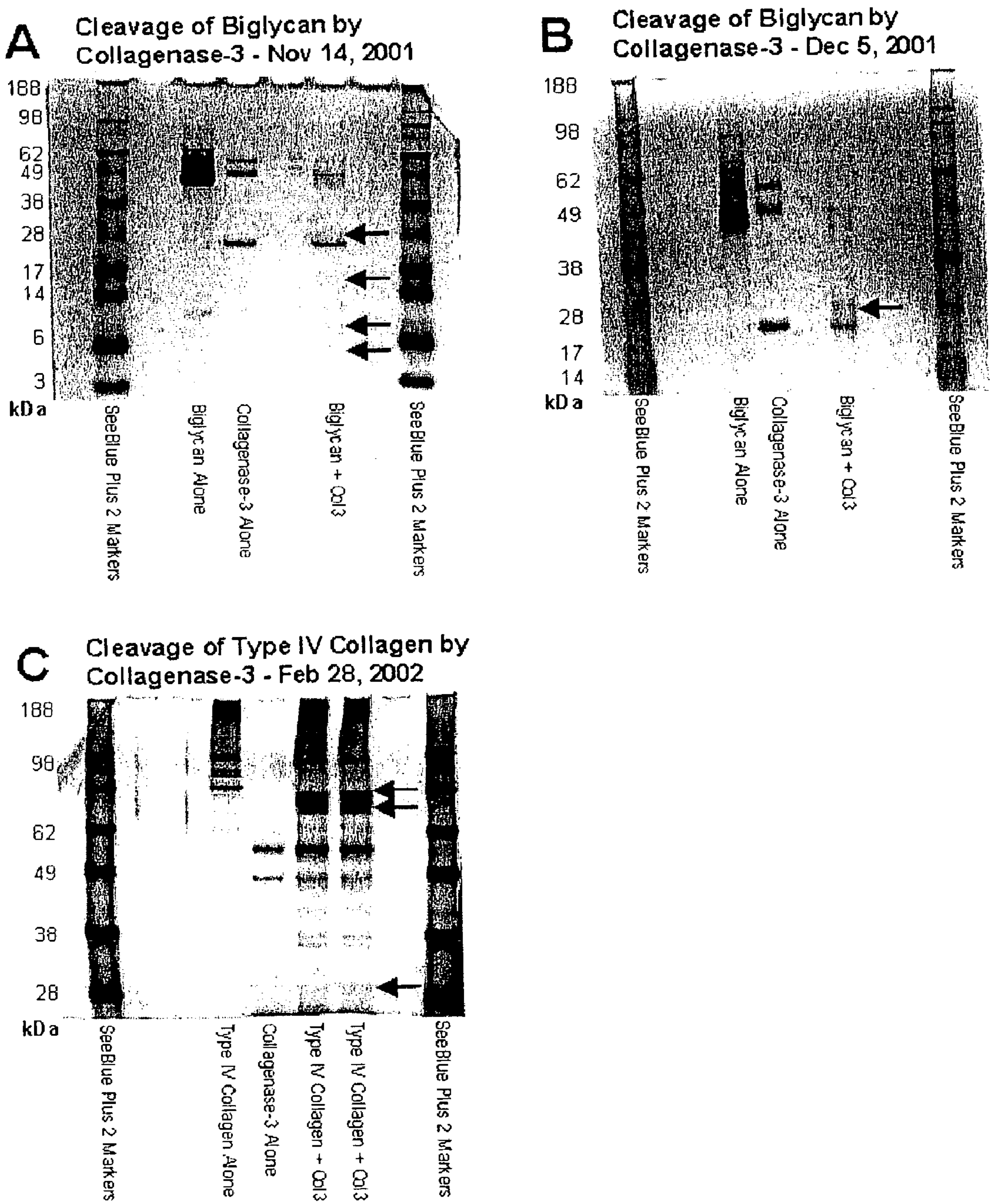
FIG. 4. (A, B) Photographs of gels showing cleavage products of biglycan digested with collagenase 3; (C) Photograph of gel showing cleavage of Type IV collagen by collagenase 3.
Figure 5:
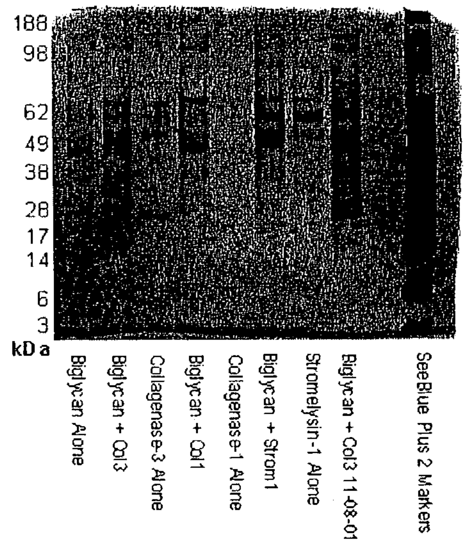
FIG. 5. (A) Photograph of gel showing cleavage of biglycan by Col-3, Col-1 and Strom-1; (B) Photograph of gel showing cleavage of biglycan by Col-3, Gel-A and GelB; (C) Photograph of gel showing cleavage of Type IV collagen by Col-3, Col-1, Strom-1 and Gel-B.
Figure 5:
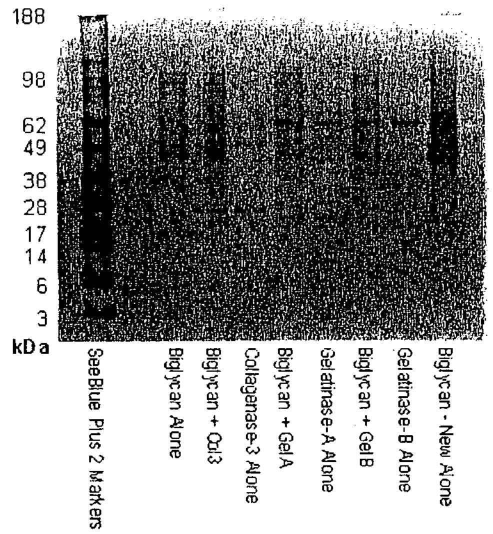
Figure 5:
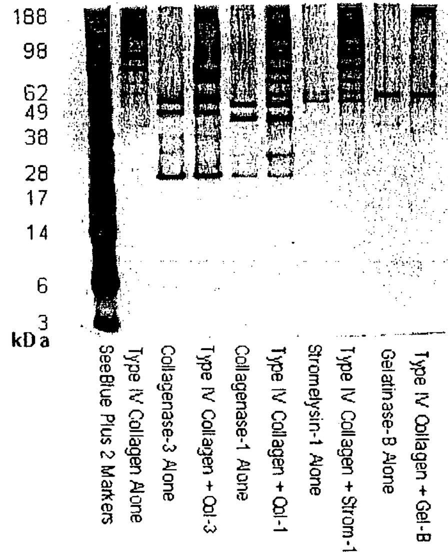

Cleavage of Biglycan and Type IV Collagen by Collagenase 3 and the MMPs and Sequence of Cleavage Products Reactions were carried out on a small scale to optimize the enzyme to full length protein ratios. For biglycan, optimum results were obtained with a ratio of 1:100 (20-40 nM col-3 and 4.3 μM biglycan in a 10 μl reaction). For type IV collagen, best results were found with a ratio of 1:50 (28 nM col-3 and 2 μM type IV collagen). For comparison with the other MMPs, an equal concentration of enzyme was used. The results are shown in FIGS. 4 and 5.

Cleavage of biglycan generated peptide fragments of 28, 17, 8, and 6 kDa (FIG. 4A) while type IV collagen digestion gave 3-4 detectable cleavage products (85 kDa, 80 kDa, 35 kDa and 28 kDa; FIG. 4B). Both collagenase 1 and gelatinase B processed type IV collagen under the conditions used in our experiments (FIG. 5C). No detectable cleavage was observed by gelatinase A in an earlier experiment. The biglycan reactions were more complex, with stromelysin 1 and gelatinase B being able to degrade this proteoglycan. However, each enzyme reaction yielded a different processing pattern, suggesting that the cleavage sites were unique. In FIGS. 5A and 5B are the cleavage reactions performed with collagenase 3, stromelysin 1, gelatinase A and gelatinase B.

Sequencing results with cleavage products generated from biglycan and type IV collagen. Sequencing of the 28 kDa for biglycan yielded a complex result as the sample was contaminated with the 27 kDa collagenase 3 fragment (FIG. 4A). However, we were able to deduce, that the N-terminus begins with amino acid 125, and is PKG*VFSGLRN (SEQ ID NO: 70), the predicted cleavage site from the phage display results in Deng et al. (2000). This finding was confirmed by a second experiment (FIG. 4B) where gel separation of the collagenase 3 fragment was achieved. In addition, we obtained sequence data on the 6 kDa fragment of biglycan. Its sequence is HKYA*LVLVNNK (beginning with amino acid 146) (SEQ ID NO: 71), and was not predicted from the previous phage display results.

With type IV collagen, we obtained sequence information from two digestion products. For the peptide at ~85 kDa (FIG. 4C), no exact sequence found to match Type IV collagen. This is possibly due to the fact it maybe a contaminant in the Type IV collagen preparation. For the peptide at ~80 kDa (FIG. 4C), a possible match was found for the sequence SXGPXGI (SEQ ID NO: 72), which corresponds to the following sequence found in Alpha-3 type Type IV collagen chain precursor (isoforms 1-5): SPGPMGI (SEQ ID NO: 72). The cleavage site, FPG*SPGPMGI (SEQ ID NO: 73) is between amino acids Glycine 1146 and Serine 1147. The star indicates where the cleavage occurs. Cleavage at this site will generate a ~40 kDa fragment. Therefore, if cleavage occurs at this site, the 40 kDa fragment will have to migrate as a dimer. Other cleavage sites that matched the sequence SXGPXGI (SEQ ID NO: 72), gave extremely high molecular weight proteins. For the protein at ~28 kDa, a match was found for the sequence XSGAXXXXGAPGIFXL (SEQ ID NO: 74), which corresponds to the following sequence found in Alpha-2 Type IV collagen chain precursor: ISGAPGDKGAPGIFGL (SEQ ID NO: 75). The cleavage site, PSN*ISGAPGDKGAPGIGFL (SEQ ID NO: 76), is between amino acids Asparagine 1275 and Isoleucine 1276.

Example 6

Generation of Neo-epitope Antibodies for Substrate Cleavage Products

A protein that is internally cleaved in half by a protease gives two protein fragments as products. The uncleaved protein has one amino terminus and one carboxy terminus. After cleavage, each of the two fragments also has an amino terminus and a carboxy terminus. On the first fragment containing the same amino terminus as the uncleaved protein, the new carboxy terminus of that fragment resulted from cleaved of the entire protein by the protease. This new carboxy terminus is considered to be a new epitope or "neo-epitope." Hence, one can raise antibodies to this "neo-epitope" and antibodies that specifically react with this neo-epitope can identify the fragments of the protein cleaved with a specific protease. By measuring the amount of the uncleaved protein and the amount of the cleaved protein fragment that reacts with the anti-neo-epitope antibodies, the amount of proteolytic activity toward a substrate protein can be measured.

Anti-neo-epitope antibodies can be produced via a number of methods such as those found in "Using Antibodies: A Laboratory Manual" by Ed Harlow and David Lane (Cold Spring Harbor Laboratory Press, Cold Spring Harbor, N.Y., 1999) and Marolewski, A. E. et al. (1998) Biochemical Journal 333: 573-579, which are herein incorporated by reference. In one method, a hypothetical protein with the sequence (in standard single letter amino acid abbreviations) is:

CADEFGHIKLM (SEQ ID NO: 77)

where A is the amino terminal amino acid residue and M is the carboxy terminal amino acid residue is cleaved by a specific protease to give 2 protein fragments (products) with the following sequences:

Fragment #1: CADEFG (SEQ ID NO: 78)
Fragment #2: HIKLM (SEQ ID NO: 79).

To produce antibodies to the new carboxy terminal epitope ending with G, the peptide CADEFG (SEQ ID NO: 78) would be synthesized on an automated peptide synthesizer by standard FMOC or other suitable synthetic chemistries. This synthetic CADEFG (SEQ ID NO: 78) peptide would be coupled to a standard carrier protein such as BSA (Bovine Serum Albumin) by cross-linking the C residue of the peptide to C residues within the BSA by standard cross-linking reagents for di-sulphide bond formation (PIERCE catalog and Using Antibodies book). Then, the complex of BSA with coupled CADEFG (SEQ ID NO: 78) peptide would be injected into rabbits in complete Freunds adjuvant followed by boosts of peptide in incomplete Freunds adjuvant on a regular schedule as set forth by a commercial supplier such as COCALICO BIOLOGICALS, INC™ (Reamstown, Pa.). Antibodies that specifically react with the carboxy-terminus of the CADEFG (SEQ ID NO: 78) peptide are "neo-epitope" antibodies. Like other anti-protein antibodies, these antibodies typically react only these specific neo-epitopes containing the CADEFG (SEQ ID NO: 78) sequence.

Similar methods may be performed using any of the substrates and cleavage products disclosed herein.

Example 7

Multiple Substrates with Simultaneous Equations

The use of multiple substrates and simultaneous equations to determine enzyme concentrations in multiple enzyme fluids to the inventors' knowledge has not been previously reported. The assay may be performed to calculate the concentration of any enzymes or proteins or other substances in a mixed sample where suitable substrates or selective binding ligands are available. When applied to determining MMP enzyme activities, a number of different substrates are used, each being most selective for one particular enzyme. The number of substrates used would equal the number of enzymes expected to be prevalent in the biological fluid in question, or the number of enzymes to be measured.

For instance, if only Col-3, Gel-A, and Strom-1 are prevalent in the fluid, then three substrates, one selective for each of those enzymes would be used in the assay. A sample of the biological fluid would be divided into 3 portions (6 if duplicating wells), and each portion would be exposed to one of the 3 substrates. The response of each of the 3 substrates versus time would be collected and analyzed after the experiment to yield the concentration of all 3 enzymes. Essentially, one is formulating 3 simultaneous equations in 3 unknowns, which provides a single, unique solution.

The multiple enzyme multiple substrate assay provides 2 distinct benefits. First, enzyme concentrations for a multiple enzymes would be provided. This information could be used to correlate disease state with a variety of enzyme levels instead of just one. Second, since the approach essentially calculates the contribution of all enzymes to the total activity, and does not assume that all activity is due to a single enzyme, increased accuracy is possible. Third, the assay provides one option for overcoming some inherent difficulties in assays such as those that detect MMP enzymes, where different enzymes may exhibit cross reactivity for a particular substrate.

For instance, a difficulty in determining Collagenase-3 levels in biological fluids is trying to assess how much activity is due to Collagenase-3 versus another MMP. While developing substrates that are more selective for Col-3 than they are for the other MMPs is helpful, other MMP enzymes may still be selected at a low level. If Col-3 were the only source of activity in the fluid, the problem would be simple, and a selective substrate would not even be necessary. Concerning substrate selectivity, let us look at an example. For argument sake, assume that Substrate X has a Selectivity of 5 when comparing Col-3 and Gel-A. In other words, it produces 5 times as much product when reacted with equal amounts of Col-3 and Gel-A for an equal period of time. Let us say that 1 nM Col-3 produces 100 counts in 1 hour, and 1 nM Gel-A produces 20 counts. Now, we test a Biological Fluid, and it produces 100 counts in 1 hour. There are an infinite number of combinations of concentrations Col-3 and Gel-A that could produce 100 counts. For example, the fluid could contain:

1 nM Col-3 only
5 nM Gel-A only
0.5 nM Col-3 and 2.5 nM Gel-A
etc.

Now, let us look at the biological side of the problem. Let us assume that the enzymes, for which we are trying to determine concentrations, are considered disease markers. In the simplest approach, one might assume that a person without a disease has none of the marker, and with the disease they have a measurable concentration. Let us say that the disease Arthritis typically produces a concentration M of Col-3, and the disease Diabetes typically produces a concentration N of Gel-A. Now if we look at a sample Biological Fluid, and the patient has Diabetes and not Arthritis, there is infinitely more Gel-A than Col-3 (N/0.0). If we test that fluid with our Substrate X, no matter how good its selectivity for Col-3 over Gel-A, if we assume the measurable activity is due solely to Col-3, we have an infinite error in our estimate. If the patient has both Arthritis and Diabetes, then the ratio of Col-3 to Gel-A is M/N. If we let M/N equal 1, and assume all activity is due to Col-3, then we have a built in 20% overestimate in the assay. Mathematically, one could say:

$$\text{Percent Overestimate in All Col-3 Assumption} = (1/S_{C3GA})*(1/C_{C3GA})*100$$

where, $S_{C3GA}$=Selectivity of Col-3 over Gel-A for Substrate X
$C_{C3GA}$=Concentration of Col-3 over Concentration of Gel-A in Biological Fluid (M/N)

Looking at this formula, one can see that the Percent Overestimate can get very large if $S_{C3GA}$ or $C_{C3GA}$ gets small. Because large selectivities do not ensure completely accurate measurement of Col-3 levels, we devised other approaches to improve our measurement accuracies:

- Prior knowledge of Enzyme Levels in Biological Fluids
- Pulling out Col-3 with a Selective Anti-body
- Using Multiple Substrates, each one Selective for a particular MMP
- Using Multiple Inhibitors, each one Selective for a particular MMP
- Using Multiple Inhibitors and Substrates, each one Selective for a particular MMP Prior Knowledge of Enzyme Levels in Biological Fluids.

If prior knowledge tells us the range of possible levels of MMPs in the Biological Fluids, then we can determine the Substrate Selectivity required for a given level of accuracy. However, complete enzyme levels for many (if not all) disease states would be required to ensure accurate results.

Pulling Out Col-3 with a Selective Antibody

If we are only interested in Col-3 levels, this technique seems most direct. Here we would run the sample "with and without" the Col-3 antibody, and assume that the difference in activity levels is due to Col-3 alone. Then, we compare that activity level with that seen in a standard curve of Col-3 concentrations. While the lab technique may be more complex (incubation with antibody, washing, etc.), the analysis and accuracy may be better.

If we are only looking for Col-3, then we only need one standard curve for comparison. The difficulty, however, is developing the technique to ensure complete and selective Antibody pullout. We have attempted this technique with mixed results. The Amersham COL-3 KIT®, for example, gives readings that are independent of antibody addition. This is likely due to non-specific binding of proteins to the plate. When we attempted an immunoprecipitation of collagenase-3 from the biological fluids, we also obtained non-specific binding of most of the proteins to the Protein G beads (used to pull out the Col-3/Antibody complex). Note also that this technique can be extended to as many specific MMP enzymes as desired by using antibodies selective for each MMP. However, the commercially available AMERSHAM kits are not very sensitive and are not completely specific for a given MMP.

Using Multiple Substrates, Each One Selective for a Particular MMP

In this technique, a number of different substrates are used, each being most selective for one particular MMP. The number of substrates used would equal the number of MMPs expected to be prevalent in the biological fluid in question. For instance, if only Col-3, Gel-A, and Strom-1 are prevalent in the fluid, then three substrates, one selective for each of those MMPs would be used in the assay. A sample of the biological fluid would be divided into 3 portions (6 if duplicating wells), and each portion would be exposed to one of the 3 substrates. The response of each of the 3 substrates versus time would be collected and analyzed after the experiment to yield the concentration of all 3 enzymes. Essentially, one is formulating 3 simultaneous equations in 3 unknowns, which provides a single, unique solution.

One underlying assumption of this multiple substrate approach is that the response of the individual enzymes to the total activity is additive. This is probably valid provided there is an excess of substrate. In this case, the individual enzymes are not competing for the same substrate molecule, but instead, each enzyme molecule has plenty of substrate molecules available for conversion. One might equate this to increasing the concentration of a single enzyme. For instance, if we have 1 nM Strom-1, and add a second aliquot of 1 nM Strom-1 to the same well, we get 2 nM Strom-1, which shows roughly twice the activity as 1 nM Strom-1.

This multiple substrate approach may provide 2 distinct benefits. First and foremost, enzyme concentrations for a multiple enzymes would be provided. This information could be used to correlate disease state with a variety of enzyme levels instead of just one. Secondly, since the approach essentially calculates the contribution of all enzymes to the total activity, and does not assume that all activity is due to a single enzyme, increased accuracy is possible.

Two Enzymes/Two Substrates+Gelatin

We first tested this multiple substrate approach using 2 enzymes and 2 substrates, Col-3 and Gel-A, and FlSub1 (+Gelatin) and FlSub3 (+Gelatin). A variety of combinations of concentrations of Col-3 and Gel-A were placed in wells. These concentration combinations were made in duplicate. Then, to one of the wells FlSub1+Gelatin was added, and to the other FlSub3+Gelatin was added. Other wells contained standard curves of Col-3 and Gel-A versus FlSub1+Gelatin and FlSub3+Gelatin.

The sequence of events in the analysis was: importation of the fluorescence vs time data, subtracting the background fluorescence from the total fluorescence in the well to give the net fluorescence, calculation of the slope of the net fluorescence vs time curve, calculation of the slope and intercept of the equation representing the slope of the net fluorescence vs time curve vs the enzyme concentration, and finally, formulation and solution of the two equations in two unknowns. The basic system equations could be written as:

$$\Sigma S_{ij} C_j = S_i$$

where, $S_i$=Slope of the Net Fluorescence vs Time Curve for the Well Containing all of the Enzymes Combined, Reacted with Substrate i $S_{ij}$=Slope of the Slope of the Net Fluorescence vs Time Curve vs Enzyme Concentration for Enzyme j Reacted with Substrate i $C_j$=Concentration of Enzyme j.

Here, $$S_{C3FS1} C_{C3} + S_{GAFS1} C_{GA} = S_{FS1}$$

$$S_{C3FS3} C_{C3} + S_{GAFS3} C_{GA} = S_{FS3}$$

where, $S_{FS1}$=Slope of the Net Fluorescence vs Time Curve for the Well Containing Col-3 and Gel-A Combined, Reacted with Fluorescence Substrate 1

$S_{FS3}$=Slope of the Net Fluorescence vs Time Curve for the Well Containing Col-3 and Gel-A Combined, Reacted with Fluorescence Substrate 3

$S_{C3FS1}$=Slope of the Slope of the Net Fluorescence vs Time Curve vs Enzyme Concentration for Enzyme Col-3, Reacted with Fluorescence Substrate 1

$S_{GAFS1}$=Slope of the Slope of the Net Fluorescence vs Time Curve vs Enzyme Concentration for Enzyme Gel-A, Reacted with Fluorescence Substrate 1

$S_{C3FS3}$=Slope of the Slope of the Net Fluorescence vs Time Curve vs Enzyme Concentration for Enzyme Col-3, Reacted with Fluorescence Substrate 3

$S_{GAFS3}$=Slope of the Slope of the Net Fluorescence vs Time Curve vs Enzyme Concentration for Enzyme Gel-A, Reacted with Fluorescence Substrate 3

$C_{C3}$=Concentration of Enzyme Collagenase-3

$C_{GA}$=Concentration of Enzyme Gelatinase-A.

After the fluorescence vs time curves were recorded and analyzed, the following results were shown:

When the ACTUAL concentration of Col-3 was HIGH, and Gel-A was LOW, the CALCULATED concentration of Col-3 was HIGH, and Gel-A was LOW.

When the ACTUAL concentration of Col-3 was LOW, and Gel-A was HIGH, the CALCULATED concentration of Col-3 was LOW, and Gel-A was HIGH.

When the ACTUAL concentration of Col-3 was HIGH, the CALCULATED concentration of Col-3 was quite accurate (within roughly 10%).

When the ACTUAL concentration of Col-3 was LOW, the CALCULATED concentration of Col-3 was not very accurate.

When the ACTUAL concentration of Gel-A was HIGH, the CALCULATED concentration of Gel-A was quite accurate (within roughly 15%).

When the ACTUAL concentration of Gel-A was LOW, the CALCULATED concentration of Gel-A was not very accurate.

Overall, the accuracy of the calculated Col-3 concentrations were better than the Gel-A concentrations. This may reflect that fact that both FlSub1 and FlSub3 are really designed as Col-3 substrates. They do vary in their selectivities for Gel-A, but they both produce more fluorescence per nM of Col-3 than they do per nM of Gel-A, possibly as much as 70 times greater activity.

Figure 6A:
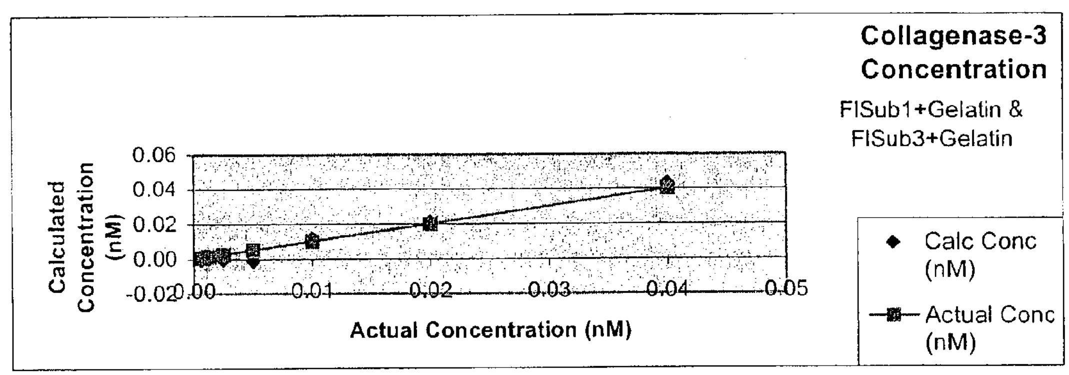
FIG. 6. (A) Graph showing calculated concentration of Col-3 vs actual concentration following measurements with FlSub1 (+Gelatin) and FlSub3 (+Gelatin); (B) Graph showing calculated concentration of Gel-A vs actual concentration following measurements with FlSub1 (+Gelatin) and FlSub3 (+Gelatin).
Figure 6B:
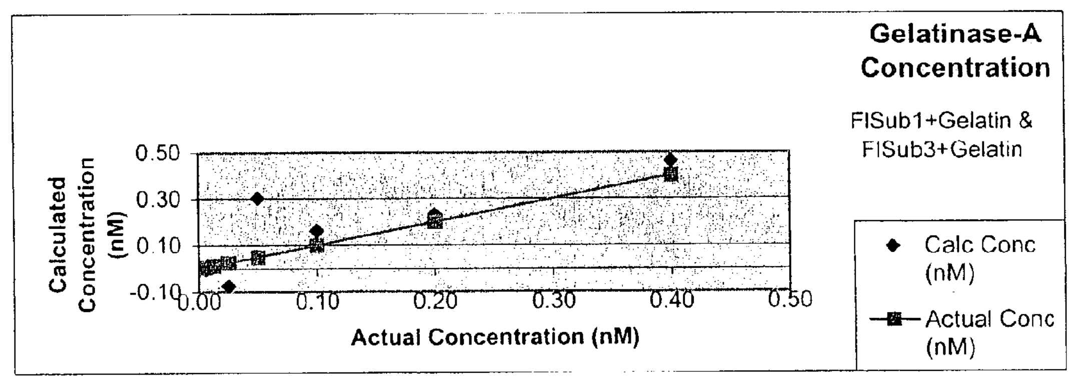

In summary, with only the Fluorescence versus Time curves of the enzyme mixtures and the enzyme standard curves, this system can discern whether a well contains high levels of Col-3 and low levels of Gel-A, or vice versa (see Table 8 below and FIG. 6). The system can distinguish whether activity is due to Col-3 or Gel-A.

TABLE 8

Actual vs Calculated Concentrations of Col-3 and Gel-A Using Two Substrate System + Gelatin

| Enzyme 1 - Collagenase-3 | | | Enzyme 2 - Gelatinase-A | | |
|---|---|---|---|---|---|
| Actual Conc (nM) | Calc Conc (nM) | Fraction of Actual Conc (fraction) | Actual Conc (nM) | Calc Conc (nM) | Fraction of Actual Conc (fraction) |
| 0.0400 | 0.0432 | 1.08 | 0.0063 | −0.0010 | −0.16 |
| 0.0200 | 0.0213 | 1.06 | 0.0125 | 0.0107 | 0.86 |
| 0.0100 | 0.0117 | 1.17 | 0.0250 | −0.0749 | −3.00 |
| 0.0050 | −0.0012 | −0.24 | 0.0500 | 0.3026 | 6.05 |
| 0.0025 | −0.0003 | −0.12 | 0.1000 | 0.1625 | 1.62 |
| 0.0013 | 0.0001 | 0.09 | 0.2000 | 0.2307 | 1.15 |
| 0.0006 | −0.0004 | −0.57 | 0.4000 | 0.4626 | 1.16 |

Two Enzymes/Two Substrates (Without Gelatin)

Figure 7:
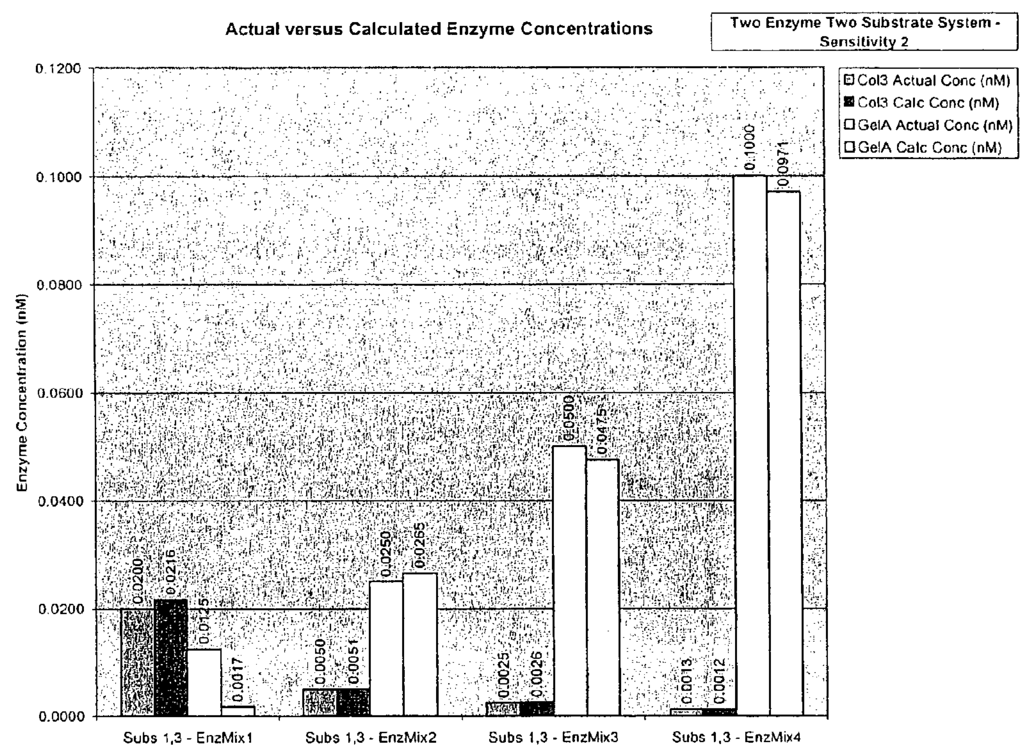
FIG. 7. Bar graph comparing the calculated concentrations of Collagenase-3 and Gelatinase-A to the actual values for 4 different multiple enzyme samples.
Figure 8:
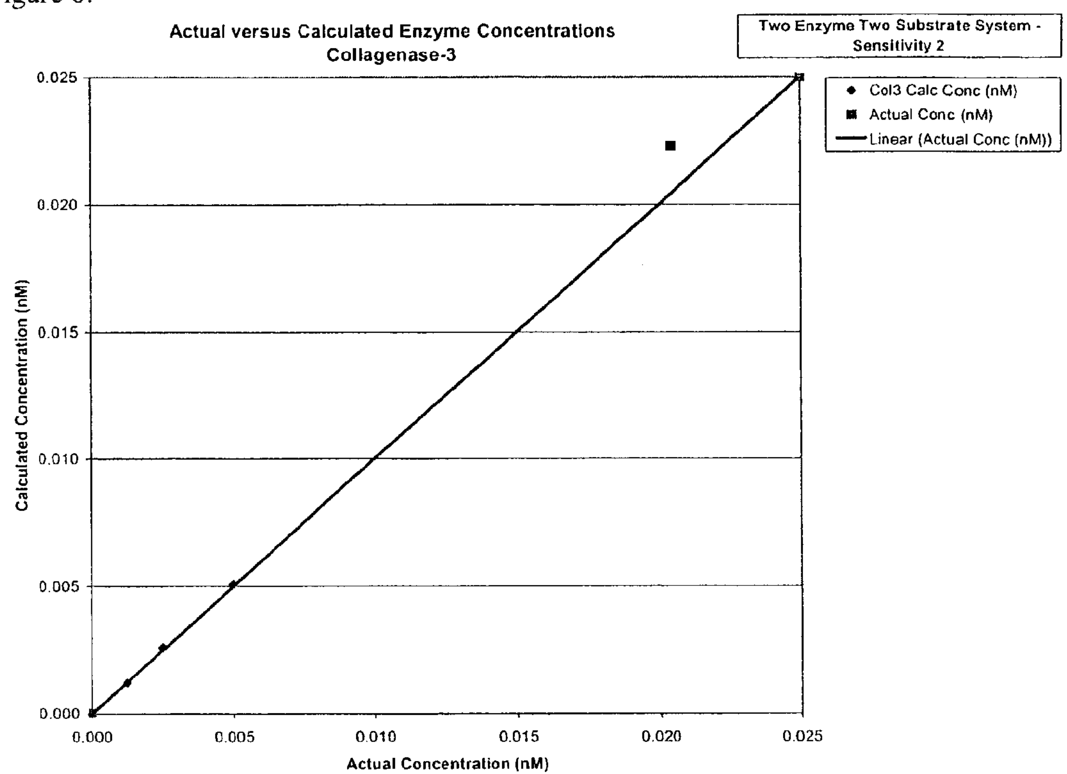
FIG. 8. Graph comparing the calculated concentrations of Collagenase-3 to the actual values for 4 different multiple enzyme samples.
Figure 9:
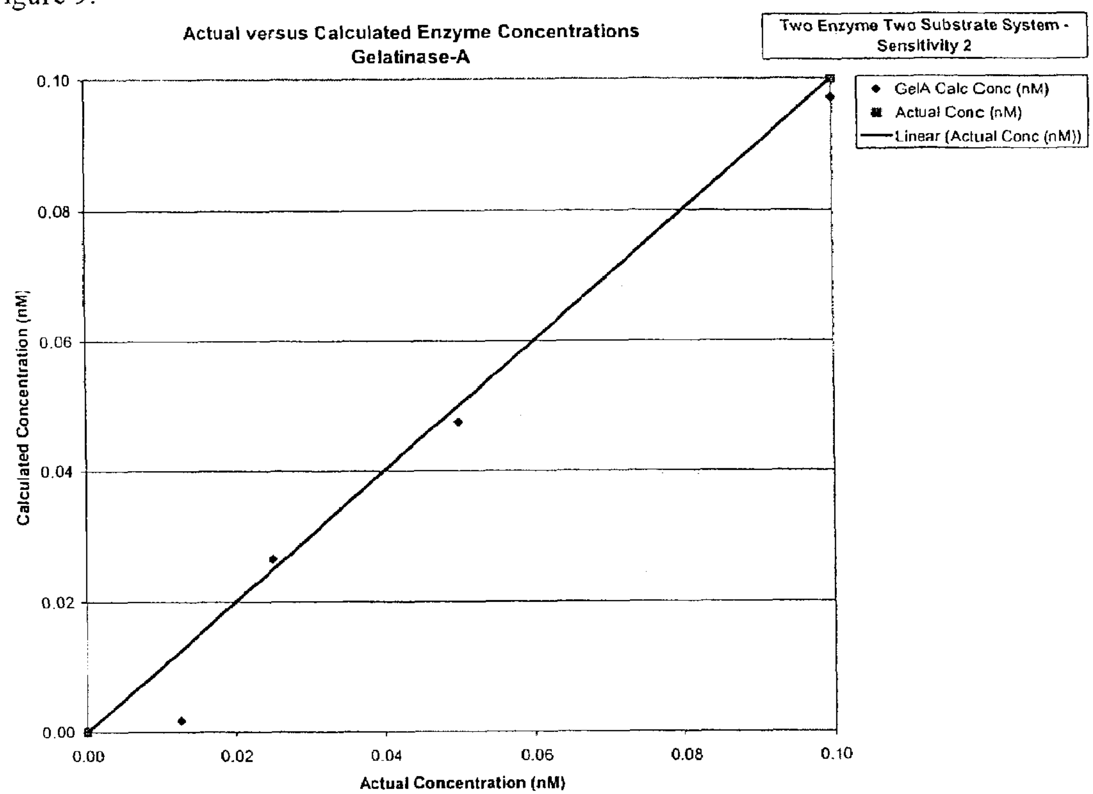
FIG. 9. Graph comparing the calculated concentrations of Gelatinase-A to the actual values for 4 different multiple enzyme samples.

We next tested whether the two substrates used in the above example could be used to accurately determine collagenase 3 and gelatinase 3 levels in the absence of gelatin. The results were impressive. Table 9 and FIGS. 7-9 depict the actual concentrations of collagenase 3 and gelatinase A in the mixed sample versus the concentrations calculated using the methods described above. For instance, in FIG. 7, if the system worked perfectly, the height of each adjacent pair of bars would be identical. With the exception of the lowest concentration of Gelatinase-A, the errors for every calculation are in the 2 to 8 percent range. The error may be largest at the lowest Gelatinase-A concentrations because Substrates 1 and 2 are both specific for Collagenase-3. That is, they produce higher activity per unit of Collagenase-3 than they do per unit of Gelatinase-A.

TABLE 9

Actual vs Calculated Concentrations of Collagenase 3 and Gelatinase A Using Substrates 1 and 3 (in the Absence of Gelatin)

| | Enzyme 1 - Collagenase-3 | | | Enzyme 2 - Gelatinase-A | | |
|---|---|---|---|---|---|---|
| Substrate Mixtures Analyzed and the Analysis Technique Used | Actual Conc (nM) | Calc Conc (nM) | Fraction of Actual Conc (fraction) | Actual Conc (nM) | Calc Conc (nM) | Fraction of Actual Conc (fraction) |
| Subs 1,3 | 0.0200 | 0.0216 | 1.08 | 0.0125 | 0.0017 | 0.14 |
| Subs 1,3 | 0.0050 | 0.0051 | 1.02 | 0.0250 | 0.0265 | 1.06 |
| Subs 1,3 | 0.0025 | 0.0026 | 1.04 | 0.0500 | 0.0475 | 0.95 |
| Subs 1,3 | 0.0013 | 0.0012 | 0.98 | 0.1000 | 0.0971 | 0.97 |

Using Multiple Inhibitors, Each One Selective for a Particular MMP

In this technique, a number of different inhibitors are used, each being selective for one particular MMP. The number of inhibitors used would equal the number of MMPs expected to be prevalent in the biological fluid in question. For instance, if only Col-3, Gel-A, and Strom-1 are prevalent in the fluid, then three inhibitors, one selective for each of those MMPs would be used in the assay. A sample of the biological fluid would be divided into 3 portions (6 if duplicating wells), and each portion would be exposed to one of the 3 inhibitors. The response of each of the 3 substrates versus time would be collected and analyzed after the experiment to yield the concentration of all 3 enzymes.

If the inhibitors are completely effective (fully inhibit their target enzyme) and are completely selective (do not inhibit the other MMPs in the fluid), then the calculation of the concentration of each enzyme is very simple. One would simply take the difference of the activity of a sample with and without the selective inhibitor, and compare that to the activity of a standard curve for the enzyme in question. If the inhibitors are not completely effective (do not fully inhibit their target enzyme) and are not completely selective (cause some inhibition of the other MMPs in the fluid), then the calculation of the concentration of each enzyme could be accomplished through the use of simultaneous equations which take into account the inhibition of each inhibitor on each enzyme.

Using Multiple Inhibitors and Substrates, Each One Selective for a Particular MMP In this technique, a number of different inhibitors and substrates are used, each being selective for one particular MMP. This technique could produce increased accuracy over using only a selective inhibitor or only a selective substrate. For example, suppose we have a biological fluid with equal concentrations of Col-3 and Gel-A. Next, suppose we are looking for Col-3 levels in the fluid. We have a substrate, $S_{C3}$, that is 10 times as selective for Col-3 as it is for Gel-A. Next, suppose we have an inhibitor, $I_{GA}$, that inhibits Gel-A activity by 90%, i.e. only 10% of the Gel-A activity remains. Now, if we place both $S_{C3}$ and $I_{GA}$ in a well with the biological fluid, then only $1/10^{th}$ of 10% of the activity (1%) is due to Gel-A. While this technique runs into the same issues as just using a selective substrate, in that there might be much higher levels of Gel-A in the fluid than Col-3, it still would increase accuracy over using just a selective substrate.

What is claimed:

1. An isolated substrate for collagenase 3 consisting of a peptide sequence selected from the group consisting of: GPLGMRG (SEQ ID NO:3), GPINLHG (SEQ ID NO:4), GPSELKG (SEQ ID NO:5), PHPFRG (SEQ ID NO:6), GPHPFRG (SEQ ID NO:7), GPSGIHV (SEQ ID NO:8), VTPYNMRG (SEQ ID NO:9), GPLQFRG (SEQ ID NO:10), GPKGMRG (SEQ ID NO:11), GPYGMRA (SEQ ID NO:12), GPKGITS (SEQ ID NO:13), GPRPFRG (SEQ ID NO:14), GPLSISG (SEQ ID NO:15), GPMSYNG (SEQ ID NO:16), GPLSIQD (SEQ ID NO:17), GPSGIHL (SEQ ID NO:18), GPVNLHG (SEQ ID NO:19), PSGIHL (SEQ ID NO:20), GPFGLKG (SEQ ID NO:21), GPHPMRG (SEQ ID NO:22), GPLQMRG (SEQ ID NO:23), DEGPMGLKC(Me)YLG (SEQ ID NO:24), GPVNLHGR (SEQ ID NO:25), VC(Me)PKGITSXVFR (SEQ ID NO:26), SYPSGIHLC(Me)LQR (SEQ ID NO:27), GPLGLHG (SEQ ID NO:28), GPLGFRG (SEQ ID NO:29), GPLGFRV (SEQ ID NO:30), GPLPFHV (SEQ ID NO:31), GPSPFHV (SEQ ID NO:32), GPSPLHG (SEQ ID NO:33), GPVNFRV (SEQ ID NO:34), GPAPFRG (SEQ ID NO:35), GPAPFRV (SEQ ID NO:36), GPAPLHG (SEQ ID NO:37), GPLPFRG (SEQ ID NO:38), GPLPFRV (SEQ ID NO:39), GPSPFRG (SEQ ID NO:40), GPAPLHV (SEQ ID NO:41) and GPLPLHG (SEQ ID NO:43).

2. The peptide substrate of claim 1, wherein said substrate has improved selectivity for collagenase 3 over at least one competing matrix metalloproteinase (MMP) enzyme.

3. The peptide substrate of claim 2, wherein said competing MMP enzyme is selected from the group consisting of gelatinase A, gelatinase B, collagenase 1 and stromelysin 1.

4. The peptide substrate of claim 1, wherein said substrate is attached to at least one detectable label.

5. The peptide substrate of claim 4, wherein said label is selected from the group consisting of Dnp, Dab, Flu, NBD, DMC, AMCA and EDANS.

6. A diagnostic kit for calculating the amount of collagenase 3 activity in a biological sample comprising one or more peptide substrates of claim 1.

7. The diagnostic kit of claim 6, further comprising one or more agents selected from the group consisting of (a) one or more inhibitors of non-MMLP activities, (b) one or more inhibitors of MMP activities, (c) one or more inhibitors of non-collagenase 3 MMP activities, (d) one or more activators of MMP activities, (e) one or more further substrates specific for collagenase 3, (f) one or more further substrates specific for a MMP other than collagenase 3, and (g) any one or more of collagenase 3, collagenase 1, gelatinase A, gelatinase B and stromelysin for use as calibration standards.

8. The diagnostic kit of claim 7, wherein said one or more activators of MMP activity are selected from the group consisting of APMA, proteolytic enzymes of the furin family and membrane bound MMPs (MT-MMPs).

9. The diagnostic kit of claim 7, wherein said one or more inhibitors of non-collagenase 3 MMP activities is selected from the group consisting of gelatin, type I collagen, type II collagen and fibronectin.

* * * * *